US011155798B2

United States Patent
Jump et al.

(10) Patent No.: US 11,155,798 B2
(45) Date of Patent: *Oct. 26, 2021

(54) ENZYME COMPOSITION AND USES THEREOF

(71) Applicant: NOVOZYMES A/S, Bagsvaerd (DK)

(72) Inventors: Joseph Jump, Franklinton, NC (US); Nathaniel Kreel, Franklinton, NC (US); Jeremy Saunders, Franklinton, NC (US); Michael John Akerman, Franklinton, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/567,167

(22) Filed: Sep. 11, 2019

(65) Prior Publication Data

US 2019/0390183 A1 Dec. 26, 2019

Related U.S. Application Data

(62) Division of application No. 14/915,484, filed as application No. PCT/US2014/052905 on Aug. 27, 2014, now Pat. No. 10,450,551.

(60) Provisional application No. 61/971,936, filed on Mar. 28, 2014, provisional application No. 61/944,933, filed on Feb. 26, 2014, provisional application No. 61/872,180, filed on Aug. 30, 2013.

(51) Int. Cl.

| C12P 7/06 | (2006.01) |
|---|---|
| C12P 7/14 | (2006.01) |
| C12N 9/24 | (2006.01) |
| C12N 9/50 | (2006.01) |
| C12N 9/48 | (2006.01) |
| C12N 9/30 | (2006.01) |
| C12N 9/42 | (2006.01) |
| C12N 9/58 | (2006.01) |
| C12P 19/14 | (2006.01) |
| C13K 1/06 | (2006.01) |
| C12P 19/02 | (2006.01) |
| C12N 9/28 | (2006.01) |
| C12N 9/34 | (2006.01) |

(52) U.S. Cl.
CPC .......... *C12N 9/242* (2013.01); *C12N 9/2417* (2013.01); *C12N 9/2428* (2013.01); *C12N 9/2434* (2013.01); *C12N 9/2437* (2013.01); *C12N 9/50* (2013.01); *C12N 9/58* (2013.01); *C12P 7/06* (2013.01); *C12P 7/14* (2013.01); *C12P 19/02* (2013.01); *C12P 19/14* (2013.01); *C12Y 302/01003* (2013.01); *C13K 1/06* (2013.01); *C12Y 302/01001* (2013.01); *C12Y 302/01004* (2013.01); *Y02E 50/10* (2013.01)

(58) Field of Classification Search
CPC .......... C12N 9/52; C12N 9/2147; C12N 9/58; C12N 9/2428; C12P 7/06
See application file for complete search history.

(56) References Cited

U.S. PATENT DOCUMENTS

| 4,514,496 | A | 4/1985 | Yoshizumi |
|---|---|---|---|
| 8,048,657 | B2 | 11/2011 | Breneman |
| 8,227,221 | B2 | 7/2012 | Soong |
| 8,557,541 | B2 * | 10/2013 | Landvik .................. C12P 19/02 |
| | | | 435/41 |
| 9,303,074 | B2 | 4/2016 | Schnorr |
| 9,677,095 | B2 * | 6/2017 | Deinhammer ....... C12N 9/2428 |
| 9,951,323 | B2 | 4/2018 | Matsui |
| 10,260,058 | B2 | 4/2019 | Wogulis |
| 2012/0214196 | A1 | 8/2012 | Landvik |

FOREIGN PATENT DOCUMENTS

| WO | 03/066826 A2 | 8/2003 |
|---|---|---|
| WO | 04/080923 A2 | 9/2004 |
| WO | 04/081193 A2 | 9/2004 |
| WO | 2006/069289 A2 | 6/2006 |
| WO | 2006/069290 A2 | 6/2006 |
| WO | 207/144424 A2 | 12/2007 |
| WO | 2009/149283 A1 | 12/2009 |
| WO | 2011/066576 A1 | 6/2011 |
| WO | 2011/068803 A1 | 6/2011 |
| WO | 2013/028928 A1 | 2/2013 |
| WO | 2013/055676 A1 | 4/2013 |

OTHER PUBLICATIONS

Juhasz et al, 2005, Process Biochemistry 40(11), 3519-3525.
WO 2007-144424—EBI Accession No. AOF63221.
WO 2007-144424—EBI Accession No. AOF63222.

* cited by examiner

*Primary Examiner* — Maryam Monshipouri
(74) *Attorney, Agent, or Firm* — David Fazzolare

(57) ABSTRACT

The invention relates to enzyme compositions comprising a glucoamylase, an alpha-amylase, and optionally a cellulolytic composition and/or a protease. The invention also relates to the use thereof in processes of producing sugars and/or fermentation products from starch-containing material by saccharifying and/or fermenting starch-containing material at a temperature below the initial gelatinization temperature.

15 Claims, No Drawings
Specification includes a Sequence Listing.

ENZYME COMPOSITION AND USES THEREOF

CROSS-REFERENCE TO RELATED APPLICATIONS

This application is a divisional of U.S. application Ser. No. 14/915,484 filed Feb. 29, 2016, now U.S. Pat. No. 10,450,551, which is a 35 U.S.C. 371 national application of PCT/US2014/052905 filed Aug. 27, 2014, which claims priority or the benefit under 35 U.S.C. 119 of U.S. provisional application Nos. 61/872,180, 61/944,933 and 61/971,936 filed Aug. 30, 2013, Feb. 26, 2014 and Mar. 28, 2014, respectively, the contents of which are fully incorporated herein by reference.

TECHNICAL FIELD

The present invention relates to enzyme compositions and processes of producing sugars and/or fermentation products from starch-containing materials using such enzyme compositions.

BACKGROUND ART

Processes of producing sugars and fermentation products, such as ethanol, from starch-containing materials are well-known in the art and used commercially today.

When producing fermentation products, such as ethanol, starch is conventionally converted into dextrins using a liquefying enzyme (e.g., *Bacillus* alpha-amylase) at temperatures above the initial gelatinization temperature of starch to above 100° C. The generated dextrins are hydrolyzed into sugars using a saccharifying enzyme (e.g., glucoamylase) and fermented into the desired fermentation product using a fermenting organism such as a yeast strain derived from *Saccharomyces cerevisiae*. Typically hydrolysis and fermentation are done in a simultaneous saccharification and fermentation (SSF) step.

Another type of process is also used commercially today. Starch is converted into dextrins at temperatures below the initial gelatinization temperature of starch and hydrolyzed into sugars during SSF. This type of process is referred to as a raw starch hydrolysis (RSH) process, or alternatively a "one-step process" or "no cook" process.

U.S. Pat. No. 4,514,496 concerns a process for producing alcohol by mixing a ground starchy material with mashing liquor without cooking, adding a saccharifying enzyme preparation derived from a *Rhizopus* sp., and adding an alcoholic fermenting yeast, and fermenting the slurry.

WO2003/066826 discloses a method for producing an alcohol by contacting a carbon substrate and at least one substrate-converting enzyme to produce an intermediate, and contacting said intermediate with at least one intermediate-converting enzyme.

WO 2004/080923 concerns a process for production of an alcohol product comprising the sequential steps of providing a slurry comprising water and granular starch; holding said slurry in the presence of an acid alpha-amylase and a glucoamylase at a temperature of 0° C. to 20° C. below the initial gelatinization temperature of said granular starch for a period of 5 minutes to 12 hours; holding said slurry in the presence of an acid alpha-amylase and a glucoamylase and a yeast at a temperature between 10° C. and 35° C. for a period of 20 to 250 hours to produce ethanol. A xylanase, cellulase and phytase may be present during the holding steps.

WO2004/081193 concerns a process for producing ethanol from plant material, comprising reducing the plant material to produce material comprising starch, saccharifying the starch, without cooking, with an enzyme composition, and fermenting the incubated starch to yield a composition comprising at least 15 vol-% ethanol.

WO2006/069289 concerns glucoamylases derived from *Trametes cingulata*, *Pachykytospora papyracea*, and *Leucopaxillus giganteus* and the use thereof in a process for producing a fermentation product from starch-containing material at a temperature below the initial gelatinization temperature.

WO 2011/068803 discloses glucoamylase derived from *Gloeophyllum sepiarium*, *Gloeophyllum trabeum*, or *Gloeophyllum abietinum* and the use thereof in processes of producing a fermentation product from starch-containing material.

The present invention is concerns enzyme compositions suitable for raw starch hydrolysis processes and the use of such enzyme compositions in such processes.

SUMMARY OF THE INVENTION

Enzyme Composition of the Invention

The invention relates to enzyme composition comprising a number of enzyme activities and the use thereof in processes of producing sugars and/or fermentation products, such as especially ethanol. The enzyme composition of the invention may be a blend of a number of difference enzyme activities. The enzyme activities may be of the same or difference origin.

In the first aspect the present invention relates enzyme compositions comprising glucoamylase and alpha-amylase, and optionally protease.

In a preferred embodiment the enzyme composition comprises *Gloeophyllum* glucoamylase, preferably *Gloeophyllum trabeum* glucoamylase and an alpha-amylase.

In a preferred embodiment the alpha-amylase is derived from *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein.

In an especially preferred embodiment the enzyme composition comprises the *Gloeophyllum trabeum* glucoamylase shown in SEQ ID NO: 18 herein having one or more of the following substitutions: S95P, A121P, especially S95P+A121P; and an alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N.

In another embodiment the enzyme composition comprises a glucoamylase derived from a strain of the genus *Pycnoporus*, in particular a strain of *Pycnoporus sanguineus*, such as a strain described in WO 2011/066576 (SEQ ID NOs 2, 4 or 6). In a preferred embodiment the enzyme composition comprises the glucoamylase shown in SEQ ID NO: 4 in WO 2011/066576 or SEQ ID NO: 17 herein and an alpha-amylase.

In a preferred embodiment the alpha-amylase is derived from *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein.

In an especially preferred embodiment the enzyme composition comprises the *Pycnoporus sanguineus* glucoamylase shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein, and an alpha-amylase derived from *Rhizomucor pusillus* with an *Aspergillus niger* glucoamylase linker and starch-binding domain (SBD), preferably the one shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having one or more of the following substitutions: G128D, D143N, especially G128D+D143N.

In a preferred embodiment the present invention relates enzyme compositions comprising a
  i) glucoamylase;
  ii) alpha-amylase;
  iii) cellulolytic enzyme composition;
  iv) optionally protease.

In an especially preferred embodiment the enzyme composition comprises the *Gloeophyllum trabeum* glucoamylase shown in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18, preferably having one or more of the following substitutions: S95P, A121P, especially S95P+A121P; and an alpha-amylase derived from *Rhizomucor pusillus* with an *Aspergillus niger* glucoamylase linker and starch-binding domain (SBD), preferably the one shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having one or more of the following substitutions: G128D, D143N, especially G128D+D143N, and a cellulolytic enzyme composition derived from *Trichoderma reesei* further comprising *Thermoascus aurantiacus* GH61A polypeptide having cellulolytic enhancing activity (e.g., SEQ ID NO: 2 in WO 2005/074656 or SEQ ID NO: 9 herein) and *Aspergillus fumigatus* beta-glucosidase (e.g., SEQ ID NO: 2 of WO 2005/047499 or SEQ ID NO: 8 herein), or a cellulolytic enzyme composition derived from *Trichoderma reesei* further comprising *Penicillium emersonii* GH61A polypeptide, e.g., the one disclosed as SEQ ID NO: 2 in WO 2011/041397 or SEQ ID NO: 10 herein, and *Aspergillus fumigatus* beta-glucosidase, e.g., the one disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* CBH I, e.g., the one disclosed as SEQ ID NO: 6 in WO2011/057140 and SEQ ID NO: 6 herein, and *Aspergillus fumigatus* CBH II, e.g., the one disclosed as SEQ ID NO: 18 in WO 2011/057140 and as SEQ ID NO: 7 herein.

In another especially preferred embodiment the enzyme composition comprises the *Pycnoporus sanguineus* glucoamylase shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17, and an alpha-amylase derived from *Rhizomucor pusillus* with an *Aspergillus niger* glucoamylase linker and starch-binding domain (SBD), preferably the one shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having one or more of the following substitutions: G128D, D143N, especially G128D+D143N, and a cellulolytic composition derived from *Trichoderma reesei* further comprising *Thermoascus aurantiacus* GH61A polypeptide having cellulolytic enhancing activity (e.g., SEQ ID NO: 2 in WO 2005/074656 or SEQ ID NO: 9 herein) and *Aspergillus fumigatus* beta-glucosidase (e.g., SEQ ID NO: 2 of WO 2005/047499 or SEQ ID NO: 8 herein), or a cellulolytic composition derived from *Trichoderma reesei*, preferably further comprising *Penicillium emersonii* GH61A polypeptide, e.g., the one disclosed as SEQ ID NO: 2 in WO 2011/041397 or SEQ ID NO: 10 herein, and *Aspergillus fumigatus* beta-glucosidase, e.g., the one disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* CBH I, e.g., the one disclosed as SEQ ID NO: 6 in WO2011/057140 and SEQ ID NO: 6 herein, and *Aspergillus fumigatus* CBH II, e.g., the one disclosed as SEQ ID NO: 18 in WO 2011/057140 and as SEQ ID NO: 7 herein.

In an embodiment a protease is comprised in the enzyme composition of the invention. In a preferred embodiment the protease is a metallo protease or a serine protease.

In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 5 herein.

In an embodiment the protease is the mature sequence from *Meripilus giganteus* protease 3 (peptidase family S53 protease) concerned in Example 2 in WO 2014/037438 and shown as SEQ ID NO: 20 herein. In an embodiment the protease is the mature protease 3 sequence from *Meripilus giganteus* shown as SEQ ID NO: 19 herein and SEQ ID NO: 5 in WO 2014/037438.

In a preferred embodiment the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15 (mg EP (Enzyme Protein) glucoamylase: mg EP (Enzyme Protein) alpha-amylase).

Process of the Invention

In a second aspect the invention relates to processes of producing fermentation products, such as especially ethanol, from starch-containing material, such as granular starch, comprising:
  (i) saccharifying a starch-containing material at a temperature below the initial gelatinization temperature; and
  (ii) fermenting using a fermentation organism;
  wherein saccharification and/or fermentation is done in the presence of the following enzymes: glucoamylase and alpha-amylase, and optionally protease.

In a preferred embodiment the following enzymes are present and/or added during saccharification and/or fermentation: the *Gloeophyllum trabeum* glucoamylase shown in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18, preferably one having one or more of the following substitutions: S95P, A121P, especially S95P+A121P, and an alpha-amylase.

In a preferred embodiment the alpha-amylase is derived from *Rhizomucor pusillus* with an *Aspergillus niger* glucoamylase linker and starch-binding domain (SBD), disclosed as V039 in Table 5 in WO 2006/069290 or SEQ ID NO: 13 herein.

In another preferred embodiment the following enzymes are present and/or added during saccharification and/or fermentation: the *Gloeophyllum trabeum* glucoamylase shown in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, preferably one having one or more of the following substitutions: S95P, A121P, especially S95P+A121P, and alpha-amylase derived from *Rhizomucor pusillus* with an *Aspergillus niger* glucoamylase linker and starch-binding domain (SBD), preferably the one shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably one having one or more of the following substitutions: G128D, D143N, especially G128D+D143N.

In another preferred embodiment the following enzymes are present and/or added during saccharification and/or fermentation: the *Pycnoporus sanguineus* glucoamylase shown in SEQ ID NO: 17 herein and an alpha-amylase.

In a preferred embodiment the alpha-amylase is derived from *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, preferably one having one or more of the following substitutions: G128D, D143N, especially G128D+D143N.

In an embodiment a protease is present and/or added during saccharification and/or fermentation. In a preferred embodiment the protease is a metallo protease or a serine protease. In an embodiment the metallo protease is derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and shown as SEQ ID NO: 20 herein. In an embodiment the protease is the mature protease 3 sequence from *Meripilus giganteus* shown as SEQ ID NO: 19 herein and SEQ ID NO: 5 in WO 2014/037438. In a preferred embodiment the invention relates to processes of producing fermentation products, such as especially ethanol, from starch-containing material, such as granular starch, comprising:

(i) saccharifying a starch-containing material at a temperature below the initial gelatinization temperature; and (ii) fermenting using a fermentation organism;

wherein saccharification and/or fermentation is done in the presence of the following enzymes:
i) glucoamylase;
ii) alpha-amylase;
iii) cellulolytic enzyme composition;
iv) optionally protease.

In another preferred embodiment the following enzymes are present and/or added during saccharification and/or fermentation: the *Gloeophyllum trabeum* glucoamylase shown in SEQ ID NO: 18 herein, preferably one having one or more of the following substitutions: S95P, A121P, especially S95P+A121P, and alpha-amylase derived from *Rhizomucor pusillus* with an *Aspergillus niger* glucoamylase linker and starch-binding domain (SBD), preferably the one shown in SEQ ID NO: 13 herein, preferably one having one or more of the following substitutions: G128D, D143N, especially G128D+143N, and a cellulolytic enzyme composition derived from *Trichoderma reesei*, preferably further comprising *Thermoascus aurantiacus* GH61A polypeptide having cellulolytic enhancing activity (e.g., SEQ ID NO: 2 in WO 2005/074656 or SEQ ID NO: 9 herein) and *Aspergillus fumigatus* beta-glucosidase (e.g., SEQ ID NO: 2 of WO 2005/047499 or SEQ ID NO: 8 herein), or a cellulolytic enzyme composition derived from *Trichoderma reesei* further comprising *Penicillium emersonii* GH61A polypeptide, e.g., the one disclosed as SEQ ID NO: 2 in WO 2011/041397 or SEQ ID NO: 10 herein, and *Aspergillus fumigatus* beta-glucosidase, e.g., the one disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* CBH1, e.g., the one disclosed as SEQ ID NO: 6 in WO2011/057140 and SEQ ID NO: 6 herein, and *Aspergillus fumigatus* CBH II, e.g., the one disclosed as SEQ ID NO: 18 in WO 2011/057140 and as SEQ ID NO: 7 herein.

In an embodiment a protease is present and/or added during saccharification and/or fermentation. In a preferred embodiment the protease is a metallo protease or a serine protease. In an embodiment the metallo protease is derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and shown as SEQ ID NO: 20 herein, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20. In a preferred embodiment the protease is the mature protease 3 sequence from *Meripilus giganteus* shown as SEQ ID NO: 19 herein and SEQ ID NO: 5 in WO 2014/037438.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the dose of protease added is from 1-200 µg/g DS, such as from 2-100 µg/g DS, such as 3-50 µg/g DS.

In a preferred embodiment saccharification step (a) and fermentation step (b) are carried out simultaneously. In a preferred embodiment an enzyme composition described above is used in a process of the invention.

DETAILED DESCRIPTION OF THE INVENTION

The invention relates to enzyme composition comprising a number of enzyme activities and the use thereof in processes of producing sugars and/or fermentation products, such as especially ethanol. An enzyme composition of the invention is suitable for use in processes for producing sugars and/or fermentation products carried out as a raw starch hydrolysis process (i.e., no cook process) at temperatures below the initial gelatinization temperature of the starch in question. When using an enzyme composition of the invention in a raw starch hydrolysis process the yield of the fermentation product, such as ethanol, is improved compared to a corresponding process where known enzyme composition consisting of glucoamylase and alpha-amylase is used. In a preferred embodiment the yield of the fermentation product, such as ethanol, is improved compared to a corresponding process where the glucoamylase or alpha-amylase is used alone or where an enzyme composition consisting of glucoamylase from *Trametes cingulata* and alpha-amylase from *Rhizomucor pusillus* with an *Aspergillus niger* glucoamylase linker and starch-binding domain (SBD) is used.

In the first aspect the present invention relates to enzyme compositions comprising glucoamylase and alpha-amylase, and optionally protease.

In an preferred embodiment the enzyme composition comprises a *Gloeophyllum* glucoamylase, preferably *Gloeophyllum trabeum* glucoamylase, especially the *Gloeophyllum trabeum* glucoamylase shown in SEQ ID NO: 18, and an alpha-amylase.

In an embodiment the glucoamylase is derived from *Gloeophyllum trabeum*, such as the one shown in SEQ ID NO: 18 herein, or a glucoamylase selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

In a preferred embodiment the *Gloeophyllum trabeum* glucoamylase shown in SEQ ID NO: 18 herein has one of the following substitutions: V59A; S95P; A121P; T119W; S95P+A121P; V59A+S95P; S95P+T119W; V59A+S95P+A121P; or S95P+T119W+A121P, especially S95P+A121P.

In a preferred embodiment the alpha-amylase is derived from a *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein.

In an embodiment the alpha-amylase is the *Rhizomucor pusillus* alpha-amylase or the *Rhizomucor pusillus* alpha-amylase with an *Aspergillus niger* glucoamylase linker and starch-binding domain (SBD), especially one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 herein for numbering).

In an embodiment the enzyme composition comprises the *Gloeophyllum trabeum* glucoamylase, preferably the one shown in SEQ ID NO: 18 and an alpha-amylase derived from *Rhizomucor pusillus*, preferably with an *Aspergillus niger* glucoamylase linker and starch-binding domain (SBD), disclosed as V039 in Table 5 in WO 2006/069290 or SEQ ID NO: 13 herein.

In another preferred embodiment the enzyme composition comprises the *Gloeophyllum trabeum* glucoamylase, preferably the one shown in SEQ ID NO: 18 herein, especially one having one or more of the following substitutions: S95P, A121P, especially S95P+A121P (using SEQ ID NO: 13 herein for numbering); and the alpha-amylase derived from *Rhizomucor pusillus* preferably with an *Aspergillus niger* glucoamylase linker and starch-binding domain (SBD), preferably one shown in SEQ ID NO: 13 herein, preferably one having one or more of the following substitutions: G128D, D143N, especially especially G128D+D143N (using SEQ ID NO: 13 herein for numbering).

In another embodiment the enzyme composition comprises a glucoamylase derived from a strain of the genus *Pycnoporus*, in particular a strain of *Pycnoporus sanguineus*, such as a strain described in WO 2011/066576 (SEQ ID NOs 2, 4 or 6). In a preferred embodiment the enzyme composition comprises the glucoamylase shown in SEQ ID NO: 4 in WO 2011/066576 or SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein, and an alpha-amylase.

In a preferred embodiment the alpha-amylase is derived from a *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein.

In an especially preferred embodiment the enzyme composition comprises the *Pycnoporus sanguineus* glucoamylase shown in SEQ ID NO: 17 herein; or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein, and the alpha-amylase derived from *Rhizomucor pusillus* with an *Aspergillus niger* glucoamylase linker and starch-binding domain (SBD), preferably the one shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having one or more of the following substitutions: G128D, D143N, especially G128D+D143N.

In a preferred embodiment the present invention relates enzyme compositions comprising a
i) glucoamylase;
ii) alpha-amylase;
iii) cellulolytic enzyme composition;
optionally iv) protease.

In an especially preferred embodiment the enzyme composition comprises the *Gloeophyllum trabeum* glucoamylase shown in SEQ ID NO: 18 herein, preferably having one or more of the following substitutions: S95P, A121P, especially S95P+A121P; and the alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N, and a cellulolytic enzyme composition derived from *Trichoderma reesei*, preferably further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein) or a cellulolytic enzyme composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y, *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein.

In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and shown as SEQ ID NO: 20 herein or a proteaase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20 herein. In an embodiment the protease is the mature protease 3 sequence from *Meripilus giganteus* shown as SEQ ID NO: 19 herein and SEQ ID NO: 5 in WO 2014/037438 or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19 herein.

Other enzymes may also be present. The specifically contemplated enzyme components are described further below.

Cellulolytic Enzyme Composition

An enzyme composition of the invention optionally contains a cellulolytic enzyme composition. The cellulolytic enzyme composition consists of or comprises one or more cellulolytic enzymes. The cellulolytic enzyme composition may be of any origin. In a preferred embodiment the cellulolytic enzyme composition comprises cellulolytic enzymes of fungal origin.

In an embodiment the cellulolytic enzyme composition is derived from a strain of *Trichoderma*, such as *Trichoderma reesei*; or a strain of *Humicola*, such as *Humicola insolens*; or a strain of *Chrysosporium*, such as *Chrysosporium lucknowense*; or a strain of *Penicillium*, such as *Penicillium decumbens*. In a preferred embodiment the cellulolytic enzyme composition is derived from a strain of *Trichoderma reesei*.

The cellulolytic enzyme composition may comprise a beta-glucosidase, a cellobiohydrolase, and an endoglucanase.

In an embodiment the cellulolytic enzyme composition comprising one or more polypeptides selected from the group consisting of:
beta-glucosidase;
cellobiohydrolase I;
cellobiohydrolase II;
or a mixture thereof.

In a preferred embodiment the cellulolytic enzyme composition further comprises a GH61 polypeptide having cellulolytic enhancing activity. Cellulolytic enhancing activity is defined and determined as described in WO 2011/041397 (incorporated by reference).

The term "GH61 polypeptide having cellulolytic enhancing activity" means a GH61 polypeptide that enhances the hydrolysis of a cellulosic material by enzymes having cellulolytic activity. For purposes of the present invention, cellulolytic enhancing activity is determined by measuring the increase in reducing sugars or the increase of the total of cellobiose and glucose from hydrolysis of a cellulosic material by cellulolytic enzyme under the following conditions: 1-50 mg of total protein/g of cellulose in PCS (Pretreated Corn Stover), wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST™ 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (see SEQ ID NOs: 74 or 76), or *Aspergillus fumigatus*, such as one disclosed in SEQ ID NO: 2 in WO 2005/047499 or SEQ ID NO: 8 herein; or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*. In an embodiment the beta-glucosidase is from a strain of *Aspergillus*, such as a strain of *Aspergillus fumigatus*, such as *Aspergillus fumigatus* beta-glucosidase (SEQ ID NO: 8 herein), or a variant thereof, which variant comprises one or more substitutions selected from the group consisting of L89M, G91L, F100D, I140V, I186V, S283G, N456E, and F512Y; such as a variant thereof with the following substitutions:

F100D+S283G+N456E+F512Y;
L89M+G91L+I186V+I140V;
I186V+L89M+G91L+I140V+F100D+S283G+N456E+F512Y.

The parent beta-glucosidase has at least 60% identity, such as at least 70%, such as at least 80%, such as at least 90%, such as at least 95%, such as at least 96%, such as at least 97%, such as at least 98%, such as at least 99% identity to the mature polypeptide of SEQ ID NO: 8 herein.

In case the beta-glucosidase is a beta-glucosidase variant it has at least 60% identity, such as at least 70%, such as at least 80%, such as at least 90%, such as at least 95%, such as at least 96%, such as at least 97%, such as at least 98%, such as at least 99%, but less than 100% identity to the mature polypeptide of SEQ ID NO: 8 herein.

In case the cellulolytic enzyme composition, comprised in an enzyme composition of the invention, comprises a GH61 polypeptide, it may be one derived from the genus *Thermoascus*, such as a strain of *Thermoascus aurantiacus*, such as the one described in WO 2005/074656 as SEQ ID NO: 2 or SEQ ID NO: 9 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 10 herein.

In a preferred embodiment the GH61 polypeptide, such as one derived from a strain of *Penicillium* sp., is selected from the group consisting of:
(i) a GH61 polypeptide comprising the mature polypeptide of SEQ ID NO: 10 herein;
(ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.

In an embodiment the cellulolytic enzyme composition, comprised in an enzyme composition of the invention, comprises a cellobiohydrolase I (CBH I), such as one derived from a strain of the genus *Aspergillus*, such as a strain of *Aspergillus fumigatus*, such as the Cel7a CBHI disclosed in SEQ ID NO: 6 in WO 2011/057140 or SEQ ID NO: 6 herein, or a strain of the genus *Trichoderma*, such as a strain of *Trichoderma reesei*.

In a preferred embodiment the cellobiohydrolase I, such as one derived from a strain of *Aspergillus fumigatus*, is selected from the group consisting of:
(i) a cellobiohydrolase I comprising the mature polypeptide of SEQ ID NO: 6 herein;
(ii) a cellobiohydrolase I comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein.

In an embodiment the cellulolytic enzyme composition, comprised in an enzyme composition of the invention, comprises a cellobiohydrolase II (CBH II), such as one derived from a strain of the genus *Aspergillus*, such as a strain of *Aspergillus fumigatus*; such as the one disclosed as SEQ ID NO: 7 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In a preferred embodiment cellobiohydrolase II, such as one derived from a strain of *Aspergillus fumigatus*, is selected from the group consisting of:
(i) a cellobiohydrolase II comprising the mature polypeptide of SEQ ID NO: 7 herein;
(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 7 herein.

In an embodiment the cellulolytic enzyme composition, comprised in an enzyme composition of the invention, comprises a GH61 polypeptide having cellulolytic enhancing activity and a beta-glucosidase.

In an embodiment the cellulolytic enzyme composition comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, and a beta-glucosidase.

In an embodiment the cellulolytic enzyme composition, comprised in an enzyme composition of the invention, comprises a GH61 polypeptide having cellulolytic enhancing activity, a beta-glucosidase, and a CBHI.

In an embodiment the cellulolytic enzyme composition, comprised in an enzyme composition of the invention, comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, a beta-glucosidase, and a CBHI.

In an embodiment the cellulolytic enzyme composition, comprised in an enzyme composition of the invention, comprises a GH61 polypeptide having cellulolytic enhancing activity, a beta-glucosidase, a CBHI, and a CBHII.

In an embodiment the cellulolytic enzyme composition, comprised in an enzyme composition of the invention, comprises a GH61 polypeptide having cellulolytic enhancing activity derived from a strain of *Penicillium*, such as a strain of *Penicillium emersonii*, such as the one disclosed as SEQ ID NO: 2 in WO 2011/041397 or SEQ ID NO: 10 herein, a beta-glucosidase, a CBHI, and a CBHII.

In an embodiment the cellulolytic enzyme composition is a *Trichoderma reesei* cellulolytic composition, further comprising *Thermoascus aurantiacus* GH61A polypeptide (SEQ ID NO: 2 in WO 2005/074656 or SEQ ID NO: 9 herein), and *Aspergillus oryzae* beta-glucosidase fusion protein (WO 2008/057637).

In an embodiment the cellulolytic enzyme composition is a *Trichoderma reesei* cellulolytic composition, further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499 or SEQ ID NO: 8 herein).

In an embodiment the cellulolytic enzyme composition is a *Trichoderma reesei* cellulolytic composition further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, which variant has one of, preferably all of, the following substitutions: F100D, S283G, N456E, F512Y, and optionally *Aspergillus fumigatus* CBH1, e.g., the one disclosed as SEQ ID NO: 6 in WO2011/057140 and SEQ ID NO: 6 herein and *Aspergillus fumigatus* CBH II, e.g., the one disclosed as SEQ ID NO: 18 in WO 2011/057140 and as SEQ ID NO: 7 herein.

In an embodiment the cellulolytic enzyme composition, comprised in an enzyme composition of the invention, comprises one or more of the following components
(i) an *Aspergillus fumigatus* cellobiohydrolase I;
(ii) an *Aspergillus fumigatus* cellobiohydrolase II;
(iii) an *Aspergillus fumigatus* beta-glucosidase or variant thereof.

In an embodiment the *Aspergillus fumigatus* beta-glucosidase (SEQ ID NO: 8 herein), comprises one or more substitutions selected from the group consisting of L89M, G91L, F100D, I140V, I186V, S283G, N456E, and F512Y; such as a variant thereof, with the following substitutions:
F100D+S283G+N456E+F512Y;
L89M+G91L+I186V+I140V; or
I186V+L89M+G91L+I140V+F100D+S283G+N456E+F512Y.

In an embodiment the cellulolytic composition further comprises the *Penicillium* sp. GH61 polypeptide shown in SEQ ID NO: 10 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.

Glucoamylase

The enzyme composition of the invention comprises a glucoamylase. The glucoamylase may be of any origin, such as of bacterial or fungal origin.

In an embodiment the glucoamylase may be one derived from a strain of *Trametes*, such as a strain of *Trametes cingulata* (SEQ ID NO: 12 herein); or a strain of *Pachykytospora*, such as a strain of *Pachykytospora papyracea*; or a strain of *Leucopaxillus*, such as a strain of *Leucopaxillus giganteus* (all disclosed in WO 2006/069289).

In a preferred embodiment the glucoamylase, comprised in an enzyme composition of the invention, is derived from a strain of *Trametes cingulata*, such as one selected from the group consisting of:
(i) a glucoamylase comprising the mature polypeptide of SEQ ID NO: 12 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 12 herein.

In an embodiment the glucoamylase, comprised in an enzyme composition of the invention, is from a strain of *Aspergillus*, preferably *Aspergillus niger*, *Aspergillus awamori*, or *Aspergillus oryzae*; or a strain of *Trichoderma*, preferably *Trichoderma reesei*; or a strain of *Talaromyces*, preferably *Talaromyces emersonii* (SEQ ID NO: 11 herein).

In an embodiment the glucoamylase, such as one derived from a strain of *Talaromyces emersonii*, is selected from the group consisting of:
(i) a glucoamylase comprising the mature polypeptide of SEQ ID NO: 11 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 11 herein.

In another embodiment the glucoamylase is derived from a strain of *Penicillium*, such as a strain of *Penicillium oxalicum*.

In an embodiment the glucoamylase, such as one derived from a strain of *Penicillium oxalicum*, is selected from the group consisting of:
(i) a glucoamylase comprising the mature polypeptide of SEQ ID NO: 16 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

In an embodiment the glucoamylase is derived from a strain of *Gloeophyllum*, such as a strain of *Gloeophyllum sepiarium* or *Gloeophyllum trabeum*, such as one disclosed in WO 2011/068803 as any of SEQ ID NOs: 2, 4, 6, 8, 10, 12, 14 or 16. In a preferred embodiment the glucoamylase is SEQ ID NO: 2 in WO 2011/068803 or SEQ ID NO: 4 herein. In another embodiment the glucoamylase is SEQ ID NO: 18 in WO 2011/068803

In a preferred embodiment the glucoamylase, such as one derived from a strain of *Gloeophyllum sepiarium*, is selected from the group consisting of:
(i) a glucoamylase comprising the mature polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 4 herein.

In a further embodiment the glucoamylase is derived from a strain of the genus *Pycnoporus*, in particular a strain of

*Pycnoporus sanguineus*, such as a strain described in WO 2011/066576 (SEQ ID NOs 2, 4 or 6). In a preferred embodiment the glucoamylase is the one shown in SEQ ID NO: 4 in WO 2011/066576 or SEQ ID NO: 17 herein.

In a preferred embodiment the glucoamylase, such as one derived from a strain of *Pycnoporus sanguineus*, is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

In a preferred embodiment the glucoamylase, such as one derived from a strain of *Gloeophyllum trabeum*, is selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

In a preferred embodiment the *Gloeophyllum trabeum* glucoamylase shown in SEQ ID NO: 18 has one of the following substitutions: V59A; S95P; A121P; T119W; S95P+A121P; V59A+S95P; S95P+T119W; V59A+S95P+A121P; or S95P+T119W+A121P, especially S95P+A121P. In a preferred embodiment the *Gloeophyllum trabeum* glucoamylase shown in SEQ ID NO: 18 has one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 herein for numbering). All *Gloeophyllum trabeum* glucoamylase variants disclosed in co-pending application EP13165995.5 and PCT/EP2014/058692 are hereby incorporated by reference.

A variant comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 18 herein.

Alpha-Amylase

The enzyme composition of the invention comprises an alpha-amylase. The alpha-amylase may be of any origin, such as of fungal or bacterial origin. In a preferred embodiment the alpha-amylase is an acid alpha-amylase, i.e., having a pH optimum below pH 7.

In an embodiment the alpha-amylase may be derived from a strain of the genus *Rhizomucor*, preferably a strain the *Rhizomucor pusillus*, such as the one shown in SEQ ID NO: 3 in WO 2013/006756 (see e.g., Table 1 in Example 1 hereby incorporated by reference), or the genus *Meripilus*, preferably a strain of *Meripilus giganteus*.

In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 (incorporated by reference) or SEQ ID NO: 13 herein.

In a preferred embodiment the alpha-amylase is derived from a *Rhizomucor pusillus* with an *Aspergillus niger* glucoamylase linker and starch-binding domain (SBD), disclosed in WO 2013/006756 (incorporated by reference) or SEQ ID NO: 13 herein.

In an embodiment the *Rhizomucor pusillus* alpha-amylase or the *Rhizomucor pusillus* alpha-amylase with an *Aspergillus niger* glucoamylase linker and starch-binding domain (SBD) has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 herein for numbering).

In an embodiment the *Rhizomucor pusillus* alpha-amylase with an *Aspergillus niger* glucoamylase linker and starch-binding domain (SBD), is selected from the group consisting of:
(i) an alpha-amylase comprising the mature polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.

In a preferred embodiment the alpha-amylase is a variant of the *Rhizomucor pusillus* alpha-amylase with an *Aspergillus niger* glucoamylase linker and starch-binding domain (SBD), wherein the alpha-amylase variant comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity, but less than 100% to the mature polypeptide of SEQ ID NO: 13 herein.

In a preferred embodiment the alpha-amylase variant has one of the above mentioned substitutions, such as: G128D, Y141W, D143W or K192R.

In a preferred embodiment the alpha-amylase (using SEQ ID NO: 13 herein for numbering) has the following substitutions: Y141W+D143N.

In a preferred embodiment the alpha-amylase has the following substitutions: G128D+Y141W+D143N.

In a preferred embodiment the alpha-amylase has the following substitutions: G128D+Y141W+D143N+K192R;

In a preferred embodiment the alpha-amylase has the following substitutions: G128D+D143N.

A variant comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity to the mature polypeptide of SEQ ID NO: 13 herein.

Protease

An enzyme composition of the invention may optionally comprise a protease. The protease may be of any origin, such as fungal or bacterial origin. In a preferred embodiment the protease is a metallo protease. In another preferred embodiment the protease is a serine protease.

In an embodiment the protease is of fungal origin.

In an embodiment the protease, optionally comprised in an enzyme composition of the invention, is a metallo protease derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

In an embodiment the protease, such as one derived from a strain of *Thermoascus aurantiacus*, is selected from the group consisting of:
(i) a protease comprising the mature polypeptide of SEQ ID NO: 3 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

In an embodiment the protease is of bacterial origin.

In an embodiment the protease, optionally comprised in an enzyme composition of the invention, is derived from a strain of *Pyrococcus*, such as a strain of *Pyrococcus furiosus*, such as the protease shown in SEQ ID NO: 1 in U.S. Pat. No. 6,358,726 or SEQ ID NO: 5 herein.

In an embodiment the protease, such as one derived from *Pyrococcus furiosus*, is selected from the group consisting of:
(i) a protease comprising the mature polypeptide of SEQ ID NO: 5 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 5 herein.

In another preferred embodiment the protease, optionally comprised in an enzyme composition of the invention, is a serine protease, such as a peptidase family S53 protease. Serine proteases of the peptidase family S53 comprises two different types of peptidases: tripeptidyl aminopeptidases (exo-type) and endo-peptidases; as described in 1993, Biochem. J. 290:205-218 and in MEROPS protease database, release, 9.4 (31 Jan. 2011) (merops.ac.uk). The database is described in Rawlings, N. D., Barrett, A. J. and Bateman, A., 2010, "MEROPS: the peptidase database", Nucl. Acids Res. 38: D227-D233. In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and shown as SEQ ID NO: 20 herein. In an embodiment the protease is the mature protease 3 sequence from *Meripilus giganteus* shown as SEQ ID NO: 19 herein and SEQ ID NO: 5 in WO 2014/037438.

In a preferred embodiment the protease, such as *Meripilus giganteus* protease 3, is selected from the group consisting of:
(i) a protease comprising the mature polypeptide of SEQ ID NO: 19 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

In an embodiment the protease, such as *Meripilus giganteus* protease 3, is selected from the group consisting of:
(i) a protease comprising the mature polypeptide of SEQ ID NO: 20 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

Pullulanase

An enzyme composition of the invention may optionally comprise a pullulanase. The pullulanase may be of any origin, such as fungal or bacterial origin.

In an embodiment the pullulanase, optionally comprised in an enzyme composition of the invention is derived from a strain of *Bacillus* sp. such as the one shown in SEQ ID NO: 15 herein or a strain of *Bacillus deramificans*.

In an embodiment the pullulanase, such as one derived from *Bacillus* sp, is selected from the group consisting of:
(i) a pullulanase comprising the mature polypeptide of SEQ ID NO: 15 herein;
(ii) a pullulanase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.

In an embodiment the enzyme composition of the invention further comprising a pullulanase, such as a *Bacillus* sp. pullulanase and a *Talaromyces emersonii* glucoamylase and/or *Gloeophyllum sepiarium* glucoamylase.

Trehalase

According to the invention the enzyme composition may further comprise a trehalase.

The trehalase may be of any origin, such as fungal or bacterial origin.

In an embodiment the trehalase is of fungal origin, such as derived from a strain of *Trichoderma*, such as *Trichoderma reesei*, such as the one shown in SEQ ID NO: 14 herein.

In an embodiment the trehalase, such as one derived from *Trichoderma reesei*, is selected from the group consisting of:
(i) a trehalase comprising the mature polypeptide of SEQ ID NO: 14 herein;
(ii) a trehalase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 14 herein.

Pectinase

According to the invention the enzyme composition may further comprise a pectinase, such as a pectin lyase (also known as pectolyase) and/or a polygalacturonase, or a combination thereof.

The pectinase may be of any origin, such as fungal or bacterial origin.

In a preferred embodiment the pectinase is a pectin lyase (EC 4.2.2.10).

In an embodiment the pectin lyase is derived from a strain of *Aspergillus*, such as *Aspergillus niger*.

In a preferred embodiment the pectinase is a polygalacturonase (EC. 3.2.1.15). In an embodiment the polygalacturonase is derived from a strain of *Aspergillus*, such as *Aspergillus aculeatus*.

In an embodiment the pectinase is a combination of pectin lyase and polygalacturonase. In an embodiment the pectinase is a combination of pectin lyase derived from *Aspergillus niger* and polygalacturonase derived from *Aspergillus aculeatus*.

Enzyme Composition Embodiments

In an embodiment the enzyme composition of the invention comprises a fungal glucoamylase and a fungal alpha-amylase, and optionally a protease.

In a preferred embodiment the enzyme composition comprises the *Gloeophyllum trabeum* glucoamylase shown in SEQ ID NO: 18 herein having one or more of the following substitutions: S95P, A121P, preferably S95P+A121P, and an alpha-amylase, preferably an alpha-amylase derived from *Rhizomucor pusillus* with an *Aspergillus niger* glucoamylase linker and starch-binding domain (SBD), shown in SEQ ID NO: 13 herein, having one or more of the following substitutions: G128D, D143N, preferably G128D+D143N.

In another preferred embodiment the enzyme composition comprises the *Pycnoporus sanguineus* glucoamylase shown in SEQ ID NO: 17 herein; and an alpha-amylase derived from *Rhizomucor pusillus* with an *Aspergillus niger* glucoamylase linker and starch-binding domain (SBD), preferably the one shown in SEQ ID NO: 13 herein, preferably having one or more of the following substitutions: G128D, D143N, especially G128D+D143N.

In a preferred embodiment the enzyme composition comprises the *Gloeophyllum sepiarium* glucoamylase shown in SEQ ID NO: 4 herein, and an alpha-amylase, preferably an alpha-amylase derived from *Rhizomucor pusillus* with an *Aspergillus niger* glucoamylase linker and starch-binding domain (SBD), shown in SEQ ID NO: 13 herein, having one or more of the following substitutions: G128D, D143N, preferably G128D+D143N.

In a preferred embodiment the enzyme composition comprises the *Trametes cingulata* glucoamylase shown in SEQ ID NO: 11 herein, and an alpha-amylase, preferably an alpha-amylase derived from *Rhizomucor pusillus* with an *Aspergillus niger* glucoamylase linker and starch-binding domain (SBD), shown in SEQ ID NO: 13 herein, having one or more of the following substitutions: G128D, D143N, preferably G128D+D143N.

In an embodiment the enzyme composition comprises a
i) fungal glucoamylase;
ii) fungal alpha-amylase;
iii) cellulolytic enzyme composition derived from a strain of *Trichoderma reesei*, further comprising a GH61 polypeptide, beta-glucosidase, CBH I and CBH II;
iv) optionally a protease.

In an embodiment the enzyme composition of the invention comprises a
i) *Trametes cingulata* glucoamylase;
ii) *Rhizomucor pusillus* alpha-amylase, or variant thereof;
iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
iv) optionally a protease from *Thermoascus aurantiacus*, or variant thereof.

In an embodiment the enzyme composition of the invention comprises a
i) *Trametes cingulata* glucoamylase;
ii) *Rhizomucor pusillus* alpha-amylase, or variant thereof;
iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y (using SEQ ID NO: 8 herein for numbering), and optionally *Aspergillus fumigatus* CBH I and *Aspergillus fumigatus* CBH II;
iv) optionally a protease from Pyropoccus *furiosus*, preferably the one shown in.

In an embodiment the enzyme composition of the invention comprises a
i) glucoamylase derived from *Trametes cingulata*;
ii) alpha-amylase derived from *Rhizomucor pusillus* with an *Aspergillus niger* glucoamylase linker and starch-binding domain (SBD), or a variant thereof;
iii) cellulolytic enzyme composition derived from a strain of *Trichoderma reesei*;
iv) optionally a protease from *Thermoascus aurantiacus*, or a variant thereof and/or *Pyrococcus furiosus*, or *Meripilus giganteus*.

In an embodiment the enzyme composition comprises a
i) fungal glucoamylase;
ii) fungal alpha-amylase;
iii) cellulolytic enzyme composition derived from a strain of *Trichoderma reesei*, further comprising a GH61 polypeptide, beta-glucosidase CBH I and CBH II;
iv) pectinase, preferably a pectin lyase or a polygalacturonase, or a combination thereof.

In an embodiment the pectinase is a combination of pectin lyase derived from *Aspergillus niger* and polygalacturonase derived from *Aspergillus aculeatus*.

In an embodiment the pectinase is a combination of pectin lyase and polygalacturonase. In an embodiment the pectinase is a combination of pectin lyase derived from *Aspergillus niger* and polygalacturonase derived from *Aspergillus aculeatus*.

In an embodiment the enzyme composition comprises a
i) fungal glucoamylase;
ii) fungal alpha-amylase;
iii) pectinase, preferably a pectin lyase or a polygalacturonase, or a combination thereof;
iv) cellulolytic enzyme composition derived from a strain of *Trichoderma reesei*, further comprising a GH61 polypeptide, beta-glucosidase CBH I and CBH II;
v) protease.

In an embodiment the enzyme composition comprises a
i) fungal glucoamylase;
ii) fungal alpha-amylase;
iii) cellulolytic enzyme composition derived from a strain of *Trichoderma reesei*, further comprising a GH61 polypeptide, beta-glucosidase CBH I and CBH II;
iv) optionally a protease.

In an embodiment the enzyme composition of the invention comprises a
i) *Trametes cingulata* glucoamylase;
ii) *Rhizomucor pusillus* alpha-amylase, or variant thereof;
iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;

iv) pectin lyase derived from *Aspergillus niger* or polygalacturonase derived from *Aspergillus aculeatus*, or a combination thereof;

v) protease from *Thermoascus aurantiacus*, or a variant thereof, or *Pyrococcus furiosus*, or *Meripilus giganteus*.

In a preferred embodiment the enzyme composition comprises i) *Gloeophyllum trabeum* glucoamylase shown in SEQ ID NO: 18 herein having one or more of the following substitutions: S95P+A121P;

ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;

iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;

optionally iv) protease from *Thermoascus aurantiacus*, or a variant thereof.

In a preferred embodiment the enzyme composition comprises i) *Pycnoporus sanguineus* glucoamylase shown in SEQ ID NO: 17 herein;

ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;

iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;

optionally iv) protease from *Thermoascus aurantiacus*, or a variant thereof.

In a preferred embodiment the enzyme composition comprises i) *Pycnoporus sanguineus* glucoamylase shown in SEQ ID NO: 17 herein;

ii) alpha-amylase derived from *Rhizomucor pusillus* with an *Aspergillus niger* glucoamylase linker and starch-binding domain (SBD), shown in SEQ ID NO: 13 herein, having of the following substitutions: G128D+D143N;

iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;

optionally iv) protease from *Meripipus giganteus*, such as *Meripipus giganteus* protease 3.

In a preferred embodiment the enzyme composition comprises i) *Pycnoporus sanguineus* glucoamylase shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein;

ii) alpha-amylase derived from *Rhizomucor pusillus* with an *Aspergillus niger* glucoamylase linker and starch-binding domain (SBD), shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having of the following substitutions: G128D+D143N;

iii) optionally a cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y (sing SEQ ID NO: 8 herein for numbering), and optionally *Aspergillus fumigatus* CBH I and *Aspergillus fumigatus* CBH II;

iv) protease from *Meripipus giganteus*, such as *Meripipus giganteus* protease 3, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20 herein.

In a preferred embodiment the enzyme composition comprises i) *Gloeophyllum sepiarium* glucoamylase shown in SEQ ID NO: 4 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 4 herein;

ii) alpha-amylase derived from *Rhizomucor pusillus* with an *Aspergillus niger* glucoamylase linker and starch-binding domain (SBD), shown in SEQ ID NO: 13 herein, or an alpha-amylasehaving at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably having of the following substitutions: G128D+D143N;

iii) cellulolytic enzyme composition derived from a strain of *Trichoderma reesei*, preferably further comprising *Penicillium emersonii* GH61A polypeptide, *Aspergillus fumigatus* beta-glucosidase with the following substitutions: F100D, S283G, N456E, F512Y (using SEQ ID NO: 8 for numbering), and optionally *Aspergillus fumigatus* CBH I and *Aspergillus fumigatus* CBH II;

optionally iv) protease from *Thermoascus aurantiacus* shown in SEQ ID NO: 3 herein, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein, or a variant thereof.

In a preferred embodiment the enzyme composition comprises i) *Trametes cingulata* glucoamylase shown in SEQ ID NO: 12 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 12 herein;

ii) alpha-amylase derived from *Rhizomucor pusillus* with an *Aspergillus niger* glucoamylase linker and starch-binding domain (SBD), shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, having of the following substitutions: G128D+D143N;

iii) cellulolytic enzyme composition derived from a strain of *Trichoderma reesei*, preferably further comprising *Peni-

*cillium emersonii* GH61A polypeptide, *Aspergillus fumigatus* beta-glucosidase with the following substitutions: F100D, S283G, N456E, F512Y (using SEQ ID NO: 8 herein for numbering), and optionally *Aspergillus fumigatus* CBH I and *Aspergillus fumigatus* CBH II;

optionally iv) protease from *Thermoascus aurantiacus*, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein, or a variant thereof.

Process of the Invention

As mentioned above an enzyme composition of the invention may suitably be used in a raw starch hydrolysis (RSH) process for producing desired sugars and fermentation products. In RSH processes the starch does not gelatinize as the process is carried out at temperatures below the initial gelatinization temperature of the starch in question.

The desired fermentation product may in an embodiment be ethanol produced from un-gelatinized (i.e., uncooked), preferably milled, grains, such as corn, or small grains such as wheat, oats, barley, rye, rice, or cereals such as sorghum. Examples of suitable starch-containing starting materials are listed in the section "Starch-Containing Materials"-section below.

Accordingly, in this aspect the invention relates to processes of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase and alpha-amylase, and optionally a protease.

In an embodiment the glucoamylase is the *Gloeophyllum trabeum* glucoamylase shown in SEQ ID NO: 18 herein having one or more of the following substitutions: S95P, A121P, preferably S95P+A121P and the alpha-amylase derived from *Rhizomucor pusillus* with an *Aspergillus niger* glucoamylase linker and starch-binding domain (SBD), shown in SEQ ID NO: 13 herein, having one or more of the following substitutions: G128D, D143N, preferably G128D+D143N.

In a preferred embodiment the invention relates to processes of producing fermentation products from starch-containing material comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase;
  ii) alpha-amylase;
  iii) cellulolytic enzyme composition;
  iv) optionally protease.

In a preferred embodiment the enzyme may be added as an enzyme composition of the invention. In a preferred embodiment steps (a) and (b) are carried out simultaneously (i.e., one-step fermentation). However, step (a) and (b) may also be carried our sequentially.

According to this aspect of the invention a desired fermentation product, such as ethanol, may be produced without liquefying the aqueous slurry containing the starch-containing material. The process of the invention includes saccharifying (e.g., milled) starch-containing material, e.g., granular starch, below the initial gelatinization temperature, preferably in the presence of an enzyme composition of the invention. The sugars generated during saccharification can be simultaneously fermented into the desired fermentation product by suitable fermenting organism(s).

In a preferred embodiment a cellulolytic enzyme composition is one described above in the "Cellulolytic Enzyme Composition"-section. Preferably the cellulolytic enzyme composition is added to the process of the invention.

In a preferred embodiment the cellulolytic enzyme composition is comprised in an enzyme composition of the invention. According to the invention the enzymes, preferably in the form of an enzyme composition of the invention, are added to the saccharification and/or fermentation, preferably simultaneous saccharification and fermentation. It should be understood that the enzymes may also be added individually or as two, three, four or more enzyme composition. In an embodiment the glucoamylase and alpha-amylase are added as one blend composition and the cellulolytic enzyme composition and optional protease are added separately. In another embodiment the cellulolytic enzyme composition, the glucoamylase, and the alpha-amylase are added as one enzyme composition and the optional protease is added separately. All enzymes may be added as one enzyme composition comprising a glucoamylase, an alpha-amylase, optionally a cellulolytic enzyme composition, and/or a protease, and optionally other enzymes including pullulanase and/or pectinase, such as pectin lyase or polygalacturonase.

The fermentation product, such as especially a liquid fermentation product, such as ethanol, may optionally be recovered after fermentation, e.g., by distillation. Subsequent to fermentation the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovering fermentation products are well known in the art.

An example of a fermenting organism is yeast, preferably a strain of *Saccharomyces cerevisiae*. *Saccharomyces cerevisiae* may according to the invention be used for producing ethanol. Other suitable fermenting organisms are listed in the "Fermenting Organisms"-section below.

The term "initial gelatinization temperature" means the lowest temperature at which starch gelatinization commences. In general, starch heated in water begins to gelatinize between about 50° C. and 75° C. The exact temperature of gelatinization depends on the specific starch and depends on the degree of cross-linking of the amylopectin. The initial gelatinization temperature can readily be determined by the skilled artisan. The initial gelatinization temperature may vary according to the plant species, to the particular variety of the plant species as well as with the growth conditions. In context of this invention the initial gelatinization temperature of a given starch-containing material may be determined as the temperature at which birefringence is lost in 5% of the starch granules using the method described by Gorinstein. S. and Lii. C., Starch/Starke, Vol. 44 (12) pp. 461-466 (1992).

Before step (a) an aqueous slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants.

Because the process of the invention is carried out below the initial gelatinization temperature and thus no significant viscosity increase takes place, high levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolysate.

A process of the invention is conducted at a temperature below the initial gelatinization temperature, which means that the temperature at which a separate step (a) is carried out typically lies in the range between 25-75° C., such as between 30-70° C., or between 45-60° C.

In a preferred embodiment the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

In an embodiment of the invention fermentation is carried out for 30 to 150 hours, preferably 48 to 96 hours. 66.

In an embodiment fermentation is carried out so that the sugar level, such as glucose level, is kept at a low level, such as below 6 wt.-%, such as below about 3 wt.-%, such as below about 2 wt.-%, such as below about 1 wt.-%., such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 and WO2004/081193 (incorporated by reference). Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

According to the invention the enzymes or enzyme composition is added so that the glucoamylase is present in an amount of 0.001 to 10 AGU/g DS, preferably from 0.01 to 5 AGU/g DS, especially 0.1 to 0.5 AGU/g DS.

According to the invention the enzymes or enzyme composition is added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes or enzyme composition is added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes or enzyme composition is added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes or enzyme composition is added so that the protease is present in an amount of 0.0001-1 mg enzyme protein per g DS, preferably 0.001 to 0.1 mg enzyme protein per g DS. Alternatively, the protease is present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes or enzyme composition is added so that the protease is present or added in an amount in the range 1-1,000 µg EP/g DS, such as 2-500 µg EP/g DS, such as 3-250 µg EP/g DS.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is according to the invention from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the dose of protease added is from 1-200 µg/g DS, such as from 2-100 µg/g DS, such as 3-50 µg/g DS.

Starch-Containing Materials

According to the process of the invention any suitable starch-containing starting material, including granular starch (raw uncooked starch), may be used. The starting material is generally selected based on the desired fermentation product. Examples of starch-containing starting materials, suitable for use in processes of the present invention, include cereal, tubers or grains. Specifically the starch-containing material may be corn, wheat, barley, rye, milo, sago, cassava, tapioca, sorghum, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

Fermenting Organisms

According to the invention "fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product, especially ethanol. Examples of fermenting organisms include fungal organisms, such as yeast. Preferred yeast includes strains of *Saccharomyces* spp., in particular, *Saccharomyces cerevisiae*.

Fermenting organisms engineered to produce one or more enzymes, such a saccharolytic enzyme, such as glucoamylase, is also contemplated. The contemplated yeast, especially *Saccharomyces cerevisae*, may also be engineered to produce less glycerol. Examples of such yeast can be found in WO/2011/153516 (Mascoma). In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED START™ and ETHANOL RED☐ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Fermentation Products

The term "fermentation product" means a product produced by a process, including a fermentation step, of the invention using one or more fermenting organisms. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. The fermentation product, such as ethanol, obtained according to the invention, may preferably be used as fuel. However, in the case of ethanol it may also be used as potable ethanol.

Fermentation Medium

The term "fermentation medium" refers to the environment in which fermentation is carried out and which includes the fermentable substrate, that is, a carbohydrate source (e.g., glucose) that can be metabolized by the fermenting organism(s).

The fermentation medium may comprise nutrients and/or growth stimulator(s) for the fermenting organism(s). Nutrient and growth stimulators are widely used in the art of fermentation and include nitrogen sources, such as ammonia; vitamins; and minerals, or combinations thereof.

Examples of Processes of the Invention

In a preferred embodiment the process of producing a fermentation product from starch containing material of the invention, comprising:

(a) saccharifying a starch-containing material at a temperature below the initial gelatinization temperature; and (b) fermenting using a fermentation organism;

wherein saccharification and/or fermentation is done in the presence of the following enzymes:

i) glucoamylase derived from *Trametes cingulata, Gloeophyllum trabeum, Gloeophyllum sepiarium*, or *Pycnoporus sanguineus*;

ii) alpha-amylase derived from *Rhizomucor pusillus* with an *Aspergillus niger* glucoamylase linker and starch-binding domain (SBD), or a variant thereof;

iii) cellulolytic enzyme composition derived from *Trichoderma reesei*;

iv) optionally a protease from *Thermoascus aurantiacus*, or a variant thereof and/or *Pyrococcus furiosus* or *Meripilus giganteus*.

In a preferred embodiment the process of producing a fermentation product from starch containing material of the invention, comprising:

(a) saccharifying a starch-containing material at a temperature below the initial gelatinization temperature; and (b) fermenting using a fermentation organism;

wherein saccharification and/or fermentation is done in the presence of the following enzymes:

i) glucoamylase derived from *Gloeophyllum trabeum* disclosed in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, preferably with the following substitutions: S95P+A121P;

ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably with the following substitutions: G128D+D143N;

iii) cellulolytic enzyme composition derived from *Trichoderma reesei*;

iv) optionally a protease from *Thermoascus aurantiacus*, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein, or a variant thereof.

In a preferred embodiment the process of producing a fermentation product, such as ethanol, from starch containing material of the invention, comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase derived from *Gloeophyllum trabeum* disclosed in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, preferably with the following substitutions: S95P+A121P;

ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, with the following substitutions: G128D+D143N;

iii) optionally a cellulolytic enzyme composition, such as one derived from *Trichoderma reesei*;

iv) a protease from *Meripilus giganteus*, such as *Meripilus giganteus* protease 3, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20 herein.

In a preferred embodiment the process of producing a fermentation product, such as ethanol, from starch containing material of the invention, comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase derived from *Gloeophyllum trabeum* disclosed in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, with the following substitutions: S95P+A121P;

ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, with the following substitutions: G128D+D143N;

iii) cellulolytic enzyme composition derived from *Trichoderma reesei*;

iv) a protease from *Meripilus giganteus*, such as *Meripilus giganteus* protease 3, such as one disclosed in SEQ ID NO: 19 herein or SEQ ID NO: 20 herein, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 19 herein or SEQ ID NO: 20 herein, respectively.

In a preferred embodiment the process of producing a fermentation product from starch containing material of the invention, comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase derived from *Pycnoporus sanguineus* shown in SEQ ID NO: 17 herein; or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein, ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably with the following substitutions: G128D+D143N;

iii) cellulolytic enzyme composition derived from *Trichoderma reesei*;

iv) optionally a protease from *Thermoascus aurantiacus*, or a variant thereof.

In a preferred embodiment the process of producing a fermentation product from starch containing material of the invention, comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase derived from *Gloeophyllum sepiarium* shown in SEQ ID NO: 4 herein; or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 4 herein, ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, with the following substitutions: G128D+D143N;

iii) cellulolytic enzyme composition derived from *Trichoderma reesei;* iv) optionally a protease from *Thermoascus aurantiacus*, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein, or a variant thereof.

In a preferred embodiment the process of producing a fermentation product from starch containing material of the invention, comprising:
(a) saccharifying a starch-containing material at a temperature below the initial gelatinization temperature; and
(b) fermenting using a fermentation organism;
wherein saccharification and/or fermentation is done in the presence of the following enzymes:

i) glucoamylase derived from *Trametes cingulata* shown in SEQ ID NO: 12 herein; or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 12 herein, ii) alpha-amylase derived from *Rhizomucor pusillus* with an *Aspergillus niger* glucoamylase linker and starch-binding domain (SBD), or a variant thereof, shown in SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably with the following substitutions: G128D+D143N;

iii) cellulolytic enzyme composition derived from *Trichoderma reesei;* iv) optionally a protease from *Thermoascus aurantiacus*, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 3 herein, or a variant thereof.

Materials & Methods
Materials:
GtAMG:

Glucoamylase derived from *Gloeophyllum trabeum* disclosed in SEQ ID NO: 18 herein, with the following substitutions: S95P+A121P.
PsAMG:

Glucoamylase derived from *Pycnoporus sanguineus* disclosed as shown in SEQ ID NO: 4 in WO 2011/066576 and in SEQ ID NO: 17 herein.
TcAMG:

Glucoamylase derived from *Trametes cingulata* shown in SEQ ID NO: 12 herein or SEQ ID NO: 2 in WO 2006/69289
AAPE096:

Alpha-amylase derived from *Rhizomucor pusillus* with an *Aspergillus niger* glucoamylase linker and starch-binding domain (SBD) shown in SEQ ID NO: 13 herein, with the following substitutions: G128D+D143N.
Cellulase VD:

Cellulolytic composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y and *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

Protease Oxa:

Metallo protease derived from *Thermoascus aurantiacus* disclosed as the mature part of SEQ ID NO: 2 disclosed in WO 2003/048353 or the mature polypeptide of SEQ ID NO: 3 herein.

Mg Protease 3:

Serine peptidase family S53 protease from a strain of *Meripilus giganteus* concerned in Example 2 in WO 2014/037438 or SEQ ID NO: 20.

Methods:
Identity

The relatedness between two amino acid sequences or between two polynucleotide sequences is described by the parameter "identity".

For purposes of the present invention, the degree of identity between two amino acid sequences is determined by the Clustal method (Higgins, 1989, CAB/OS 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two polynucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

SIGMA Enzymatic Assay for Trehalase

One SIGMA unit will convert 1.0 micro mol of trehalose to 2.0 micro mol of glucose per minutes at pH 5.7 at 37° C. (liberated glucose determined at pH 7.5).

Glucoamylase Activity

Glucoamylase activity may be measured in Glucoamylase Units (AGU).

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

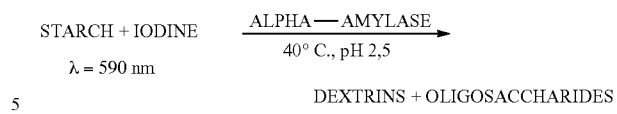

blue/violet t=23 sec. decoloration
Standard Conditions/Reaction Conditions:
Substrate: Soluble starch, approx. 0.17 g/L
Buffer: Citrate, approx. 0.03 M
Iodine (12): 0.03 g/L
$CaCl_2$: 1.85 mM
pH: 2.50±0.05
Incubation temperature: 40° C.
Reaction time: 23 seconds
Wavelength: 590 nm
Enzyme concentration: 0.025 AFAU/mL
Enzyme working range: 0.01-0.04 AFAU/mL A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Measurement of Cellulase Activity Using Filter Paper Assay (FPU Assay)

1. Source of Method 1.1 The method is disclosed in a document entitled "Measurement of Cellulase Activities" by Adney, B. and Baker, J. 1996. Laboratory Analytical Procedure, LAP-006, National Renewable Energy Laboratory (NREL). It is based on the IUPAC method for measuring cellulase activity (Ghose, T. K., Measurement of Cellulse Activities, Pure & Appl. Chem. 59, pp. 257-268, 1987.

2. Procedure 2.1 The method is carried out as described by Adney and Baker, 1996, supra, except for the use of a 96 well plates to read the absorbance values after color development, as described below.

2.2 Enzyme Assay Tubes:

2.2.1 A rolled filter paper strip (#1 Whatman; 1×6 cm; 50 mg) is added to the bottom of a test tube (13×100 mm).

2.2.2 To the tube is added 1.0 mL of 0.05 M Na-citrate buffer (pH 4.80).

2.2.3 The tubes containing filter paper and buffer are incubated 5 min. at 50° C. (±0.1° C.) in a circulating water bath.

2.2.4 Following incubation, 0.5 mL of enzyme dilution in citrate buffer is added to the tube. Enzyme dilutions are designed to produce values slightly above and below the target value of 2.0 mg glucose.

2.2.5 The tube contents are mixed by gently vortexing for 3 seconds.

2.2.6 After vortexing, the tubes are incubated for 60 mins. at 50° C. (±0.1° C.) in a circulating water bath.

2.2.7 Immediately following the 60 min. incubation, the tubes are removed from the water bath, and 3.0 mL of DNS reagent is added to each tube to stop the reaction. The tubes are vortexed 3 seconds to mix.

2.3 Blank and Controls 2.3.1 A reagent blank is prepared by adding 1.5 mL of citrate buffer to a test tube.

2.3.2 A substrate control is prepared by placing a rolled filter paper strip into the bottom of a test tube, and adding 1.5 mL of citrate buffer.

2.3.3 Enzyme controls are prepared for each enzyme dilution by mixing 1.0 mL of citrate buffer with 0.5 mL of the appropriate enzyme dilution.

2.3.4 The reagent blank, substrate control, and enzyme controls are assayed in the same manner as the enzyme assay tubes, and done along with them.

2.4 Glucose Standards 2.4.1 A 100 mL stock solution of glucose (10.0 mg/mL) is prepared, and 5 mL aliquots are frozen. Prior to use, aliquots are thawed and vortexed to mix.

2.4.2 Dilutions of the stock solution are made in citrate buffer as follows:

G1=1.0 mL stock+0.5 mL buffer=6.7 mg/mL=3.3 mg/0.5 mL

G2=0.75 mL stock+0.75 mL buffer=5.0 mg/mL=2.5 mg/0.5 mL

G3=0.5 mL stock+1.0 mL buffer=3.3 mg/mL=1.7 mg/0.5 mL

G4=0.2 mL stock+0.8 mL buffer=2.0 mg/mL=1.0 mg/0.5 mL 2.4.3 Glucose standard tubes are prepared by adding 0.5 mL of each dilution to 1.0 mL of citrate buffer.

2.4.4 The glucose standard tubes are assayed in the same manner as the enzyme assay tubes, and done along with them.

2.5 Color Development 2.5.1 Following the 60 min. incubation and addition of DNS, the tubes are all boiled together for 5 mins. in a water bath.

2.5.2 After boiling, they are immediately cooled in an ice/water bath.

2.5.3 When cool, the tubes are briefly vortexed, and the pulp is allowed to settle. Then each tube is diluted by adding 50 microL from the tube to 200 microL of ddH2O in a 96-well plate. Each well is mixed, and the absorbance is read at 540 nm.

2.6 Calculations (examples are given in the NREL document)

2.6.1 A glucose standard curve is prepared by graphing glucose concentration (mg/0.5 mL) for the four standards (G1-G4) vs. A540. This is fitted using a linear regression (Prism Software), and the equation for the line is used to determine the glucose produced for each of the enzyme assay tubes.

2.6.2 A plot of glucose produced (mg/0.5 mL) vs. total enzyme dilution is prepared, with the Y-axis (enzyme dilution) being on a log scale.

2.6.3 A line is drawn between the enzyme dilution that produced just above 2.0 mg glucose and the dilution that produced just below that. From this line, it is determined the enzyme dilution that would have produced exactly 2.0 mg of glucose.

2.6.4 The Filter Paper Units/mL (FPU/mL) are calculated as follows:

FPU/mL=0.37/enzyme dilution producing 2.0 mg glucose

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e. 25° C., pH 5.5 and 10 min. reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Determination of Maltogenic Amylase Activity (MANU)

One MANU (Maltogenic Amylase Novo Unit) may be defined as the amount of enzyme required to release one micro mole of maltose per minute at a concentration of 10 mg of maltotriose (Sigma M 8378) substrate per ml of 0.1 M citrate buffer, pH 5.0 at 37° C. for 30 minutes.

EXAMPLES

Example 1

Raw Starch Ethanol Production Using Gt AMG and AAPE096 Alpha-Amylase

Finely-ground (250 microns) raw starch slurry was generated for this experiment. Approximately 405 g yellow dent corn flour (obtained from Southeast Iowa Renewable Energy, IA, USA—ground in-house) was added to 595 g tap water and the dry solids (DS) level was determined to be 35.00%. The mash was prepared to 500 ppm urea and 3 mg/L penicillin using solutions of 200 g/L urea and 1 g/L penicillin, respectively, and adjusted to pH 4.5. Approximately 5 g of the prepared mashes were pipetted into each of preweighed 15 mL centrifuge tubes, which had holes drilled in the top. The tubes were again weighed to determine the mass of mash added.

RED START™ yeast was rehydrated, with 5.5 g of yeast placed in 100 mL of 32° C. tap water for 30 minutes. While the yeast soaked, each mash sample was dosed with glucoamylase (AMG) and alpha-amylase (AA) enzymes in the amounts and ratios according to the tables below.

Each treatment contained 6 replicates. Enzyme dosage was calculated using the following equation:

$$\text{Enz. dose (ml)} = \frac{\text{Final enz. dose } (AGU/g\ DS) \times \text{Mash weight}(g) \times \text{Solid content } (\%\ DS/100)}{\text{Conc. enzyme}(AGU/\text{ml})}$$

Water was dosed into each sample such that the total added volume of enzyme, water, yeast and acid (added at the end of the experiment) was 275 μL/5 g sample. The rehydrated yeast was dosed to 100 μL of yeast solution in each sample. The samples were placed in a water bath at 32° C. for 88 hours. Each sample was vortexed in the morning and evening of each day to ensure good mixing. At 72 hours and 88 hours of fermentation, three samples from each treatment were sacrificed for HPLC analysis. The sacrificed samples were dosed with 50 μL of 40% v/v $H_2SO_4$, vortexed, and centrifuged for 10 min. at 1462×g. Supernatant was filtered through a 0.45 um syringe filter and this was used directly for HPLC analysis. HPLC samples were analyzed on the following system.

| | |
|---|---|
| HPLC system | Agilent's 1100/1200 series with Chem station software<br>Degasser<br>Quaternary Pump<br>Auto-Sampler<br>Column Compartment/w Heater<br>Refractive Index Detector (RI) |
| Column | Bio-Rad HPX- 87H Ion Exclusion Column 300 mm × 7.8 mm parts# 125-0140<br>Bio-Rad guard cartridge cation H parts# 125-0129, Holder parts# 125-0131 |
| Method | 0.005M $H_2SO_4$ mobile phase<br>Flow rate of 0.6 ml/min<br>Column temperature - 65° C.<br>RI detector temperature - 55° C. |

The method quantifies analytes using calibration standards for dextrins (DP4+), maltotriose, maltose, glucose, fructose, acetic acid, lactic acid, glycerol and ethanol. A 4 point calibration including the origin is used.

TABLE

Broad Range AMG:AA protein dose ratio study

| Treatment | Protein Dose (μg/g DS) | % EtOH 72 Hours | % EtOH 88 Hours |
|---|---|---|---|
| 50:50 GtAMG:AAPE096 | 100 | 15.25 | 15.59 |
| 62:38 GtAMG:AAPE096 | 100 | 15.40 | 15.63 |
| 87:13 GtAMG:AAPE096 | 100 | 15.52 | 15.66 |
| 100:0 (Control) GtAMG:AAPE096 | 100 | 7.69 | 8.39 |
| 50:50 GtAMG:AAPE096 | 112 | 15.26 | 15.52 |
| 62:38 GtAMG:AAPE096 | 112 | 15.33 | 15.55 |
| 87:13 GtAMG:AAPE096 | 112 | 15.47 | 15.64 |
| 100:0 (Control) GtAMG:AAPE096 | 112 | 7.98 | 8.19 |
| 50:50 GtAMG:AAPE096 | 138 | 15.34 | 15.54 |
| 62:38 GtAMG:AAPE096 | 138 | 15.45 | 15.58 |
| 87:13 GtAMG:AAPE096 | 138 | 15.57 | 15.69 |
| 100:0 (Control) GtAMG:AAPE096 | 138 | 8.12 | 8.65 |
| 50:50 GtAMG:AAPE096 | 150 | 15.46 | 15.61 |
| 62:38 GtAMG:AAPE096 | 150 | 15.49 | 15.65 |
| 87:13 GtAMG:AAPE096 | 150 | 15.64 | 15.76 |
| 100:0 (Control) GtAMG:AAPE096 | 150 | 8.23 | 8.69 |

TABLE

Narrow Range AMG:AA protein dose ratio study

| Treatment | Protein Dose (μg/g DS) | % EtOH 88 Hours |
|---|---|---|
| 85:15 GtAMG:AAPE096 | 85 | 15.06 |
| 90:10 GtAMG:AAPE096 | 85 | 15.09 |
| 94:6 GtAMG:AAPE096 | 85 | 15.14 |
| 97:3 GtAMG:AAPE096 | 85 | 14.97 |
| 85:15 GtAMG:AAPE096 | 101 | 15.09 |
| 90:10 GtAMG:AAPE096 | 101 | 15.12 |
| 94:6 GtAMG:AAPE096 | 101 | 15.19 |
| 97:3 GtAMG:AAPE096 | 101 | 15.11 |
| 85:15 GtAMG:AAPE096 | 134 | 15.18 |
| 90:10 GtAMG:AAPE096 | 134 | 15.12 |
| 94:6 GtAMG:AAPE096 | 134 | 15.28 |
| 97:3 GtAMG:AAPE096 | 134 | 15.16 |
| 85:15 GtAMG:AAPE096 | 150 | 15.20 |
| 90:10 GtAMG:AAPE096 | 150 | 15.15 |
| 94:6 GtAMG:AAPE096 | 150 | 15.21 |
| 97:3 GtAMG:AAPE096 | 150 | 15.20 |

Example 2

Raw Starch Ethanol Production Using Gt AMG and AAPE096 Alpha-Amylase—Dose Response with and without Added Cellulase VD In this example, the AMG and AA ratio was held constant at 93:7 protein ratio, respectively and the overall dose was increased as shown in the Table. Cellulase was added to the treatments indicated. Doses are stated per gram DS.

TABLE

Dose Response of Gt AMG and AAPE096 Alpha-Amylase - With and Without Added Cellulase VD

| Treatment | Total AMG + AA Dose (μg/g DS) | % EtOH 72 Hours | % EtOH 88 Hours |
|---|---|---|---|
| Gt AMG + AAPE096 | 141 | 15.132 | 15.212 |
| Gt AMG + AAPE096 + Cellulase VD (100 μg) | 141 | 15.243 | 15.325 |
| Gt AMG + AAPE096 | 159 | 15.128 | 15.275 |
| Gt AMG + AAPE096 + Cellulase VD (100 μg) | 159 | 15.261 | 15.360 |
| Gt AMG + AAPE096 | 176 | 15.242 | 15.266 |
| Gt AMG + AAPE096 + Cellulase VD (100 μg) | 176 | 15.336 | 15.403 |
| Gt AMG + AAPE096 | 194 | 15.251 | 15.237 |
| Gt AMG + AAPE096 + Cellulase (100 μg) | 194 | 15.283 | 15.399 |
| Gt AMG + AAPE096 | 212 | 15.216 | 15.362 |
| Gt AMG + AAPE096 + Cellulase VD (100 μg) | 212 | 15.388 | 15.436 |

Example 3

Raw Starch Ethanol Production Using Gt AMG and AAPE096 Alpha-Amylase—with Cellulase VD and Protease Oxa In this example, the AMG and AA ratio was held constant at 94:6 protein ratio, respectively, at 147.9 μg total protein dose. Additional enzyme(s) in the amounts indicated were added in separate treatments and the results obtained according to the Table below.

| Treatment | % EtOH 48 Hours | % EtOH 72 Hours | % EtOH 88 Hours |
|---|---|---|---|
| GtAMG + AAPE096 | 14.33 | 15.13 | 15.36 |
| GtAMG + AAPE096 + Cellulase VD (100 μg) | 14.46 | 15.14 | 15.44 |
| GtAMG + AAPE096 + Cellulase VD (100 μg) + Protease Oxa (10 μg) | 14.84 | 15.46 | 15.80 |

Example 4

Raw Starch Ethanol Production Using TcAMG and AAPE096 Alpha-Amylase—with Cellulase VD and Protease Oxa In this example, the AMG and AA ratio was held constant at 77:23 protein ratio, respectively, at 116 μg total protein dose. Additional enzyme(s) in the amounts indicated were added in separate treatments and the results obtained according to the Table below.

| Treatment | % EtOH 72 Hours | % EtOH 88 Hours |
|---|---|---|
| TcAMG + AAPE096 | 15.03 | 15.17 |
| TcAMG + AAPE096 + Cellulase VD (100 μg) | 15.15 | 15.32 |
| TcAMG + AAPE096 + Cellulase VD (100 μg) + Protease Oxa (20 μg) | 15.31 | 15.40 |
| TcAMG + AAPE096 + Protease Oxa (20 μg) | 15.19 | 15.36 |

Example 5

Raw Starch Ethanol Production Using Ps AMG and AAPE096 Alpha-Amylase

Finely-ground (250 microns) raw starch slurry was generated for this experiment. Approximately 405 g yellow dent corn flour (obtained from Southeast Iowa Renewable Energy, IA, USA—ground in-house) was added to 595 g tap water and the dry solids (DS) level was determined to be 34.71%. The mash was prepared to 500 ppm urea and 3 mg/L penicillin using solutions of 200 g/L urea and 1 g/L penicillin, respectively, and adjusted to pH 4.5. Approximately 5 g of the prepared mashes were pipetted into each of preweighed 15 mL centrifuge tubes, which had holes drilled in the top. The tubes were again weighed to determine the mass of mash added.

RED START™ yeast was rehydrated, with 5.5 g of yeast placed in 100 mL of 32° C. tap water for 30 minutes. While the yeast soaked, each mash sample was dosed with glucoamylase (AMG) and alpha-amylase (AA) enzymes in the amounts and ratios according to the tables below.

Each treatment contained 6 replicates. Enzyme dosage was calculated using the following equation:

$$\text{Enz. dose (ml)} = \frac{\text{Final } \textit{enz.} \text{ dose } (AGU/g\ DS) \times \text{Mash weight (g)} \times \text{Solid content } (\%\ DS/100)}{\text{Conc. enzyme } (AGU/\text{ml})}$$

Water was dosed into each sample such that the total added volume of enzyme, water, yeast and acid (added at the end of the experiment) was 275 μL/5 g sample. The rehydrated yeast was dosed to 100 μL of yeast solution in each sample. The samples were placed in a water bath at 32° C. for 88 hours. Each sample was vortexed in the morning and evening of each day to ensure good mixing.

At 72 hours and 88 hours of fermentation, three samples from each treatment were sacrificed for HPLC analysis. The sacrificed samples were dosed with 50 μL of 40% v/v $H_2SO_4$, vortexed, and centrifuged for 10 min. at 1462×g. Supernatant was filtered through a 0.45 um syringe filter and this was used directly for HPLC analysis. HPLC samples were analyzed on the following system.

| | |
|---|---|
| HPLC system | Agilent's 1100/1200 series with Chem station software<br>Degasser<br>Quaternary Pump<br>Auto-Sampler<br>Column Compartment/w Heater<br>Refractive Index Detector (RI) |
| Column | Bio-Rad HPX- 87H Ion Exclusion Column 300 mm × 7.8 mm parts# 125-0140<br>Bio-Rad guard cartridge cation H parts# 125-0129, Holder parts# 125-0131 |
| Method | 0.005M $H_2SO_4$ mobile phase<br>Flow rate of 0.6 ml/min<br>Column temperature - 65° C.<br>RI detector temperature - 55° C. |

The method quantifies analytes using calibration standards for dextrins (DP4+), maltotriose, maltose, glucose, fructose, acetic acid, lactic acid, glycerol and ethanol. A 4 point calibration including the origin is used.

TABLE

Broad Range AMG:AA protein dose ratio study

| Treatment | Protein Dose (ug/g DS) | % EtOH 72 Hours | % EtOH 88 Hours |
|---|---|---|---|
| 65:35 PsAMG:AAPE096 | 75 | 14.536 | 14.982 |
| 83:17 PsAMG:AAPE096 | 75 | 14.663 | 15.067 |
| 94:6 PsAMG:AAPE096 | 75 | 14.590 | 15.029 |
| 100:0 (Control) PsAMG:AAPE096 | 75 | 6.036 | 6.463 |
| 65:35 PsAMG:AAPE096 | 94 | 14.843 | 15.126 |
| 83:17 PsAMG:AAPE096 | 94 | 14.894 | 15.174 |
| 94:6 PsAMG:AAPE096 | 94 | 14.838 | 15.177 |
| 100:0 (Control) PsAMG:AAPE096 | 94 | 6.191 | 6.639 |
| 65:35 PsAMG:AAPE096 | 131 | 14.990 | 15.231 |
| 83:17 PsAMG:AAPE096 | 131 | 15.070 | 15.200 |
| 94:6 PsAMG:AAPE096 | 131 | 15.067 | 15.237 |
| 100:0 (Control) PsAMG:AAPE096 | 131 | 6.634 | 6.943 |
| 65:35 PsAMG:AAPE096 | 150 | 15.130 | 15.268 |
| 83:17 PsAMG:AAPE096 | 150 | 15.138 | 15.308 |
| 94:6 PsAMG:AAPE096 | 150 | 15.157 | 15.326 |
| 100:0 (Control) PsAMG:AAPE096 | 150 | 6.773 | 7.094 |

TABLE

Narrow Range AMG:AA protein dose ratio study (mash % DS = 34.17%)

| Treatment | Protein Dose (ug/g DS) | % EtOH 88 Hours |
|---|---|---|
| 85:15 PsAMG:AAPE096 | 85 | 15.057 |
| 90:10 PsAMG:AAPE096 | 85 | 15.060 |
| 94:6 PsAMG:AAPE096 | 85 | 14.983 |
| 97:3 PsAMG:AAPE096 | 85 | 14.964 |

TABLE-continued

Narrow Range AMG:AA protein dose ratio study (mash % DS = 34.17%)

| Treatment | Protein Dose (ug/g DS) | % EtOH 88 Hours |
|---|---|---|
| 85:15 PsAMG:AAPE096 | 101 | 15.085 |
| 90:10 PsAMG:AAPE096 | 101 | 15.100 |
| 94:6 PsAMG:AAPE096 | 101 | 15.064 |
| 97:3 PsAMG:AAPE096 | 101 | 15.125 |
| 85:15 PsAMG:AAPE096 | 134 | 15.244 |
| 90:10 PsAMG:AAPE096 | 134 | 15.106 |
| 94:6 PsAMG:AAPE096 | 134 | 15.159 |
| 97:3 PsAMG:AAPE096 | 134 | 15.164 |
| 85:15 PsAMG:AAPE096 | 150 | 15.132 |
| 90:10 PsAMG:AAPE096 | 150 | 15.144 |
| 94:6 PsAMG:AAPE096 | 150 | 15.140 |
| 97:3 PsAMG:AAPE096 | 150 | 15.241 |

Example 6

Raw Starch Ethanol Production Using Ps AMG and AAPE096 Alpha-Amylase—Dose Response with and without Added Cellulase VD In this example, the AMG and AA ratio was held constant at 90:10 protein ratio, respectively, and the overall dose was increased as shown in the Table below. Cellulase VD and Protease Oxa was added to the treatments indicated. Doses are stated as ug enzyme protein per gram DS.

TABLE

Dose Response of Ps AMG and PE 96 with and without added Cellulase VD (mash % DS = 35.49%)

| Treatment | Total AMG + AA Dose (ug/g DS) | % EtOH 72 Hours | % EtOH 88 Hours |
|---|---|---|---|
| Ps AMG + AAPE096 | 169 | 15.86 | 16.16 |
| Ps AMG + AAPE096 + Cellulase VD (100 ug) | 169 | 15.92 | 16.17 |
| Ps AMG + AAPE096 | 198 | 15.95 | 16.15 |
| Ps AMG + AAPE096 + Cellulase VD (100 ug) | 198 | 15.98 | 16.20 |

TABLE

Ps AMG and AAPE096 with and without added Cellulase VD and Protease Oxa (mash % DS = 34.56%)

| Treatment | Total AMG + AA Dose (ug/g DS) | % EtOH 88 Hours |
|---|---|---|
| Ps AMG + PE 96 | 169 | 15.24 |
| Ps AMG + PE 96 + Cellulase VD (100 ug) | 169 | 15.41 |
| Ps AMG + AAPE096 + Cellulase VD(100 ug) + Protease Oxa (10 ug) | 169 | 15.42 |

Example 7

Raw Starch Ethanol Production Using PsAMG, AAPE096 Alpha-Amylase, and Mq Protease 3

Approximately 795 g yellow dent corn (obtained from Lincolnway Ethanol; ground in-house Turkish grind setting on Bunn coffee grinder) was added to 1205 g tap water and the dry solids (DS) level was determined to be 34.64% (see below for method). This mixture was supplemented with 3 ppm penicillin and 500 ppm urea. The slurry was adjusted to pH 4.5 with 40% $H_2SO_4$. Approximately 5 g of this slurry was added to 15 mL tubes. Each tube was dosed with enzymes according to Table 1, followed by 100 μL of rehydrated yeast (5.5 g Fermentis Ethanol Red yeast in 100 mL $H_2O$, incubated for 30 min at 32° C. with magnetic stirring). Table 2 shows the enzymes used for this experiment. Water was added to each tube to bring the total added volume (enzyme+water) to 5.3% of the initial weight of the mash. This volume correction brings all tubes in the experiment to the same total percent solids, making ethanol concentrations directly comparable between treatments.

TABLE

Dosing Scheme

| | Glucoamylase | Dose | Units | Amylase | Dose | Units | AGU/FAU-F | Protease | Dose | Units |
|---|---|---|---|---|---|---|---|---|---|---|
| 1 | TcAMG | 0.5 | AGU/gDS | AAPE096 | 0.0476 | FAU-F/g DS | 10.5 | | | |
| 2 | PsAMG | 0.7 | AGU/gDS | AAPE096 | 0.0141 | FAU-F/g DS | 49.6 | | | |
| 3 | PsAMG | 0.85 | AGU/gDS | AAPE096 | 0.0172 | FAU-F/g DS | 49.6 | | | |
| 4 | PsAMG | 1 | AGU/gDS | AAPE096 | 0.0202 | FAU-F/g DS | 49.6 | | | |
| 5 | PsAMG | 0.7 | AGU/gDS | AAPE096 | 0.0208 | FAU-F/g DS | 33.6 | | | |
| 6 | PsAMG | 0.85 | AGU/gDS | AAPE096 | 0.0253 | FAU-F/g DS | 33.6 | | | |
| 7 | PsAMG | 1 | AGU/gDS | AAPE096 | 0.0298 | FAU-F/g DS | 33.6 | | | |
| 8 | PsAMG | 0.7 | AGU/gDS | AAPE096 | 0.0331 | FAU-F/g DS | 21.2 | | | |
| 9 | PsAMG | 0.85 | AGU/gDS | AAPE096 | 0.0402 | FAU-F/g DS | 21.2 | | | |
| 10 | PsAMG | 1 | AGU/gDS | AAPE096 | 0.0473 | FAU-F/g DS | 21.2 | | | |
| 11 | PsAMG | 0.7 | AGU/gDS | AAPE096 | 0.0141 | FAU-F/g DS | 49.6 | Protease Oxa | 0.005 | mg EP/g DS |
| 12 | PsAMG | 0.85 | AGU/gDS | AAPE096 | 0.0172 | FAU-F/g DS | 49.6 | Protease Oxa | 0.005 | mg EP/g DS |
| 13 | PsAMG | 1 | AGU/gDS | AAPE096 | 0.0202 | FAU-F/g DS | 49.6 | Protease Oxa | 0.005 | mg EP/g DS |
| 14 | PsAMG | 0.7 | AGU/gDS | AAPE096 | 0.0208 | FAU-F/g DS | 33.6 | Protease Oxa | 0.005 | mg EP/g DS |
| 15 | PsAMG | 0.85 | AGU/gDS | AAPE096 | 0.0253 | FAU-F/g DS | 33.6 | Protease Oxa | 0.005 | mg EP/g DS |
| 16 | PsAMG | 1 | AGU/gDS | AAPE096 | 0.0298 | FAU-F/g DS | 33.6 | Protease Oxa | 0.005 | mg EP/g DS |
| 17 | PsAMG | 0.7 | AGU/gDS | AAPE096 | 0.0331 | FAU-F/g DS | 21.2 | Protease Oxa | 0.005 | mg EP/g DS |
| 18 | PsAMG | 0.85 | AGU/gDS | AAPE096 | 0.0402 | FAU-F/g DS | 21.2 | Protease Oxa | 0.005 | mg EP/g DS |
| 19 | PsAMG | 1 | AGU/gDS | AAPE096 | 0.0473 | FAU-F/g DS | 21.2 | Protease Oxa | 0.005 | mg EP/g DS |
| 20 | PsAMG | 0.7 | AGU/gDS | AAPE096 | 0.0141 | FAU-F/g DS | 49.6 | Mg Protease 3 | 0.005 | mg EP/g DS |
| 21 | PsAMG | 0.85 | AGU/gDS | AAPE096 | 0.0172 | FAU-F/g DS | 49.6 | Mg Protease 3 | 0.005 | mg EP/g DS |

TABLE-continued

Dosing Scheme

|    | Glucoamylase | Dose | Units   | Amylase | Dose   | Units     | AGU/FAU-F | Protease     | Dose  | Units      |
|----|--------------|------|---------|---------|--------|-----------|-----------|--------------|-------|------------|
| 22 | PsAMG        | 1    | AGU/gDS | AAPE096 | 0.0202 | FAU-F/g DS| 49.6      | Mg Protease 3| 0.005 | mg EP/g DS |
| 23 | PsAMG        | 0.7  | AGU/gDS | AAPE096 | 0.0208 | FAU-F/g DS| 33.6      | Mg Protease 3| 0.005 | mg EP/g DS |
| 24 | PsAMG        | 0.85 | AGU/gDS | AAPE096 | 0.0253 | FAU-F/g DS| 33.6      | Mg Protease 3| 0.005 | mg EP/g DS |
| 25 | PsAMG        | 1    | AGU/gDS | AAPE096 | 0.0298 | FAU-F/g DS| 33.6      | Mg Protease 3| 0.005 | mg EP/g DS |
| 26 | PsAMG        | 0.7  | AGU/gDS | AAPE096 | 0.0331 | FAU-F/g DS| 21.2      | Mg Protease 3| 0.005 | mg EP/g DS |
| 27 | PsAMG        | 0.85 | AGU/gDS | AAPE096 | 0.0402 | FAU-F/g DS| 21.2      | Mg Protease 3| 0.005 | mg EP/g DS |
| 28 | PsAMG        | 1    | AGU/gDS | AAPE096 | 0.0473 | FAU-F/g DS| 21.2      | Mg Protease 3| 0.005 | mg EP/g DS |

Actual enzyme dosages were based on the exact weight of corn slurry in each tube according to the following formula:

$$Enz.\ dose\ (\mu L) = \frac{Final\ enz.\ dose\ (mg/g\ DS) \times Mash\ weight\ (g) \times Dry\ solid\ content\ (\%\ DS) \times 1000}{Stock\ enzyme\ conc.\ (mg/ml)}$$

Tubes were incubated at 32° C. and 6 replicate fermentations of each treatment were run. All tubes were vortexed at 24, 48 and 70 hours. Three samples were sacrificed for HPLC analysis at 72 hours, and 3 at 88 hours. The HPLC preparation consisted of stopping the reaction by addition of 50 μL of 40% $H_2SO_4$, centrifuging for 10 min at 1462×g, and filtering through a 0.45 μm filter. Samples were stored at 4° C.

HPLC analysis

HPLC system—Agilent's 1100/1200 series with ChemStation software

Column—Bio-Rad HPX-87H Ion Exclusion Column 300 mm×7.8 mm parts #125-0140 Bio-Rad guard cartridge cation H parts #125-0129, Holder parts #125-0131

Method—0.005 M $H_2SO_4$ mobile phase

Flow rate of 0.6 mL/min

Column temperature—65° C.

RI detector temperature—55° C.

The method quantifies analytes using calibration standards for DP4+, DP3, DP2, glucose, fructose, acetic acid, lactic acid, glycerol and ethanol. A four point calibration including the origin is used.

Dry Solids Analysis

Approximately 3-5 g sample of corn slurry is placed onto a pre-weighed Al pan and the pan with sample is placed into a Mettler Toledo HB43-S halogen moisture analyzer (Mettler-Toledo, Columbus, Ohio). Settings on the moisture balance were as follows—Drying Program: Standard; Temperature set-point: 160° C.; Switch-off mode: free; Time interval: 30 sec.

Data were analyzed in JMP (SAS, Cary, N.C.). Treatments were compared to control with the Tukey-Kramer Honestly Significant Difference test (p<0.05).

TABLE

Percent change of ethanol produced for each protease treatment compared to the control sample (0.5 AGU/g DSTcAMG/AAPE096) after 72 and 88 hours of fermentation.

| 72 hour PsAMG/AAPE096 (No Protease) AGU/FAU-F ratio | | | |
|---|---|---|---|
| AGU dose | 49.6 | 33.6 | 21.2 |
| 0.7  | 0.81% | 0.95% | 1.40% |
| 0.85 | 1.17% | 1.86% | 1.59% |
| 1    | 1.76% | 1.40% | 1.77% |

| 72 hour PsAMG/AAPE096 + Protease Oxa AGU/FAU-F ratio | | | |
|---|---|---|---|
| AGU dose | 49.6 | 33.6 | 21.2 |
| 0.7  | 1.36% | 1.81% | 1.81% |
| 0.85 | 1.54% | 1.67% | 2.26% |
| 1    | 1.92% | 2.26% | 2.15% |

| 72 hour PsAMG/AAPE096 + Mg Protease 3 AGU/FAU-F ratio | | | |
|---|---|---|---|
| AGU dose | 49.6 | 33.6 | 21.2 |
| 0.7  | 1.81% | 1.39% | 1.77% |
| 0.85 | 2.20% | 2.27% | 2.54% |
| 1    | 2.35% | 1.98% | 2.46% |

| 88 hour PsAMG/AAPE096 (No Protease) AGU/FAU-F ratio | | | |
|---|---|---|---|
| AGU dose | 49.6 | 33.6 | 21.2 |
| 0.7  | 0.20% | 0.26%  | 0.08% |
| 0.85 | 0.02% | −0.02% | 0.15% |
| 1    | 0.68% | 0.36%  | 0.23% |

| 88 hour PsAMG/AAPE096 + Protease Oxa AGU/FAU-F ratio | | | |
|---|---|---|---|
| AGU dose | 49.6 | 33.6 | 21.2 |
| 0.7  | −0.18% | 0.55% | 0.14% |
| 0.85 | 0.82%  | 0.16% | 0.60% |
| 1    | 0.26%  | 0.74% | 0.37% |

| 88 hour PsAMG/AAPE096 + Mg Protease 3 AGU/FAU-F ratio | | | |
|---|---|---|---|
| AGU dose | 49.6 | 33.6 | 21.2 |
| 0.7  | 1.03% | 0.62% | 1.58% |
| 0.85 | 1.00% | 1.74% | 0.64% |
| 1    | 0.48% | 0.86% | 1.28% |

CONCLUSIONS

Proteases aid in increasing fermentation kinetics and final overall ethanol yields. Mg Protease 3 significantly improves ethanol production and faster fermentation rates compared to TcAMG/PE096, PsAMG/AAPE096 (No Protease) and PsAMG/AAPE096+Protease Oxa.

The Present Invention is Further Described in the Following Numbered Paragraphs:

1. An enzyme composition comprising glucoamylase and alpha-amylase, and optionally protease.
2. An enzyme composition of paragraph 1 comprising a
   i) glucoamylase;
   ii) alpha-amylase;
   iii) cellulolytic enzyme composition;
   iv) optionally protease.
3. The enzyme composition of paragraph 2, wherein the cellulolytic enzyme composition is derived from a strain of *Trichoderma*, such as *Trichoderma reesei*; a strain of *Humicola*, such as *Humicola insolens*; a strain of *Chrysosporium*, such as *Chrysosporium lucknowense*; or a strain of *Penicillium*, such as *Penicillium decumbens*.
4. The enzyme composition of paragraphs 2 or 3, wherein the cellulolytic enzyme composition is derived from a strain of *Trichoderma reesei* and *Trichoderma reesei* comprises a beta-glucosidase, a cellobiohydrolase, and an endoglucanase.
5. The enzyme composition of any of paragraphs 1-4, wherein a cellulolytic enzyme composition comprising one or more polypeptides selected from the group consisting of:
   beta-glucosidase;
   cellobiohydrolase I;
   cellobiohydrolase II;
   or a mixture thereof.
6. The enzyme composition of any of paragraphs 1-5, wherein the cellulolytic enzyme composition further comprises a GH61 polypeptide.
7. The enzyme composition of any of paragraphs 1-6, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 6 herein or an *Aspergillus fumigatus* beta-glucosidase variant disclosed in WO 2012/044915; or a strain of the genus a strain *Penicillium*, such as a strain of the *Penicillium brasilianum* disclosed in WO 2007/019442, or a strain of the genus *Trichoderma*, such as a strain of *Trichoderma reesei*.
8. The enzyme composition of any of paragraphs 1-7, wherein the beta-glucosidase is from a strain of *Aspergillus*, such as a strain of *Aspergillus fumigatus*, such as *Aspergillus fumigatus* beta-glucosidase (SEQ ID NO: 8 herein), or a variant thereof, which variant comprises one or more substitutions selected from the group consisting of L89M, G91L, F100D, I140V, I186V, S283G, N456E, and F512Y; such as a variant thereof with the following substitutions:
   F100D+S283G+N456E+F512Y;
   L89M+G91L+I186V+I140V;
   I186V+L89M+G91L+I140V+F100D+S283G+N456E+F512Y.
9. The enzyme composition of any of paragraphs 1-8, wherein the parent beta-glucosidase has at least 60% identity, such as at least 70%, such as at least 80%, such as at least 90%, such as at least 95%, such as at least 96%, such as at least 97%, such as at least 98%, such as at least 99% identity to mature polypeptide of SEQ ID NO: 8 herein.
10. The enzyme composition of any of paragraphs 1-9, wherein the beta-glucosidase variant has at least 60% identity, such as at least 70%, such as at least 80%, such as at least 90%, such as at least 95%, such as at least 96%, such as at least 97%, such as at least 98%, such as at least 99%, but less than 100% identity to mature polypeptide SEQ ID NO: 8 herein.
11. The enzyme composition of any of paragraphs 1-19, wherein the cellulolytic enzyme composition comprises a GH61 polypeptide, such as one derived from the genus *Thermoascus*, such as a strain of *Thermoascus aurantiacus*, such as the one described in WO 2005/074656 as SEQ ID NO: 2 or SEQ ID NO: 9 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 or SEQ ID NO: 10 herein.
12. The enzyme composition of paragraph 11, wherein the GH61 polypeptide, such as *Penicillium* sp. GH61 polypeptide is selected from the group consisting of:
   (i) a GH61 polypeptide comprising the mature polypeptide of SEQ ID NO: 10 herein;
   (ii) a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.
13. The enzyme composition of any of paragraphs 1-12, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 6 herein, or a strain of the genus *Trichoderma*, such as a strain of *Trichoderma reesei*.
14. The enzyme composition of any of paragraphs 1-13, wherein the cellobiohydrolase I, such as *Aspergillus fumigatus* cellobiohydrolase I, is selected from the group consisting of:
   (i) a cellobiohydrolase I comprising the mature polypeptide of SEQ ID NO: 6 herein;
   (ii) a cellobiohydrolase I comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 6 herein.
15. The enzyme composition of any of paragraphs 1-14, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 7 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

16. The enzyme composition of paragraph 15, wherein the cellobiohydrolase II, such as *Aspergillus fumigatus* cellobiohydrolase II, is selected from the group consisting of:

(i) a cellobiohydrolase II comprising the mature polypeptide of SEQ ID NO: 7 herein;

(ii) a cellobiohydrolase II comprising an amino acid sequence having at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 7 herein.

17. The enzyme composition of any of paragraphs 1-16, wherein the cellulolytic enzyme composition comprises a GH61 polypeptide having cellulolytic enhancing activity and a beta-glucosidase.

18. The enzyme composition of any of paragraphs 1-17, wherein the cellulolytic enzyme composition comprises a GH61 polypeptide having cellulolytic enhancing activity and a beta-glucosidase.

19. The enzyme composition of any of paragraphs 1-18, wherein the cellulolytic enzyme composition comprises a GH61 polypeptide having cellulolytic enhancing activity, a beta-glucosidase, and a CBHI.

20. The enzyme composition of any of paragraphs 1-19, wherein the cellulolytic enzyme composition comprises a GH61 polypeptide having cellulolytic enhancing activity, a beta-glucosidase, a CBHI, and a CBHII.

21. The enzyme composition of any of paragraphs 1-20, wherein the cellulolytic enzyme composition is a *Trichoderma reesei* cellulolytic composition, further comprising *Thermoascus aurantiacus* GH61A polypeptide (SEQ ID NO: 2 in WO 2005/074656 or SEQ ID NO: 9 herein), and *Aspergillus oryzae* beta-glucosidase fusion protein (WO 2008/057637).

22. The enzyme composition of any of paragraphs 1-21, wherein the cellulolytic enzyme composition is a *Trichoderma reesei* cellulolytic composition, further comprising *Thermoascus aurantiacus* GH61A polypeptide having cellulolytic enhancing activity (SEQ ID NO: 2 in WO 2005/074656 or SEQ ID NO: 9 herein) and *Aspergillus fumigatus* beta-glucosidase (SEQ ID NO: 2 of WO 2005/047499) or SEQ ID NO: 8 herein.

23. The enzyme composition of any of paragraphs 1-22, wherein the cellulolytic enzyme composition is a *Trichoderma reesei* cellulolytic composition further comprising *Penicillium emersonii* GH61A polypeptide disclosed in WO 2011/041397 (SEQ ID NO: 10 herein) and *Aspergillus fumigatus* beta-glucosidase (SEQ ID NO: 2 of WO 2005/047499) or SEQ ID NO: 8 herein, or a variant thereof, which variant has the following substitutions: F100D, S283G, N456E, F512Y, and optionally *Aspergillus fumigatus* CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein.

24. The enzyme composition of any of paragraphs 1-23, wherein the cellulolytic enzyme composition comprises one or more of the following components (i) an *Aspergillus fumigatus* cellobiohydrolase I;

(ii) an *Aspergillus fumigatus* cellobiohydrolase II;

(iii) an *Aspergillus fumigatus* beta-glucosidase or variant thereof.

25. The enzyme composition of paragraphs 24, wherein the *Aspergillus fumigatus* beta-glucosidase (SEQ ID NO: 8 herein), which comprises one or more substitutions selected from the group consisting of L89M, G91L, F100D, I140V, I186V, S283G, N456E, and F512Y; such as a variant thereof with the following substitutions:
F100D+S283G+N456E+F512Y;
L89M+G91L+I186V+I140V;
I186V+L89M+G91L+I140V+F100D+S283G+N456E+F512Y.

26. The enzyme composition of paragraphs 24 or 25, further comprising the *Penicillium* sp. GH61 polypeptide shown in SEQ ID NO: 10 herein; or a GH61 polypeptide comprising an amino acid sequence having at least 60%, such as at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 10 herein.

27. The enzyme composition of any of paragraphs 1-25, wherein the glucoamylase is derived from a strain of *Trametes*, such as *Trametes cingulata*; or *Pachykytospora*, such as *Pachykytospora papyracea*; or *Leucopaxillus*, such as *Leucopaxillus giganteus*.

28. The enzyme composition of any of paragraphs 1-27, wherein the glucoamylase, such as *Trametes cingulata* glucoamylase, is selected from the group consisting of:

(i) a glucoamylase comprising the mature polypeptide of SEQ ID NO: 12 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 12 herein.

29. The enzyme composition of any of paragraphs 1-28, wherein the glucoamylase is from a strain of *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*.

30. The enzyme composition of any of paragraphs 1-29, wherein the glucoamylase, such as *Talaromyces emersonii* glucoamylase, is selected from the group consisting of:

(i) a glucoamylase comprising the mature polypeptide of SEQ ID NO: 11 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 11 herein.

31. The enzyme composition of paragraph 32, wherein the glucoamylase is derived from a strain of *Penicillium*, such as a strain of *Penicillium oxalicum*.

32. The enzyme composition of any of paragraphs 1-32, wherein the glucoamylase, such as *Penicillium oxalicum* glucoamylase, is selected from the group consisting of:

(i) a glucoamylase comprising the mature polypeptide of SEQ ID NO: 16 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 16 herein.

33. The enzyme composition of any of paragraphs 1-32, wherein the glucoamylase is derived from a strain of *Gloeophyllum*, such as a strain of *Gloeophyllum sepiarium*, such as one shown in SEQ ID NO: 2 in WO 2011/068803 or SEQ ID NO: 4 herein.

34. The enzyme composition of any of paragraphs 1-33, wherein the glucoamylase, such as *Gloeophyllum sepiarium* glucoamylase, is selected from the group consisting of:
(i) a glucoamylase comprising the mature polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 2 in WO 2011/068803 or SEQ ID NO: 4 herein.
35. The enzyme composition of any of paragraphs 1-34, wherein the glucoamylase is derived from a strain of *Gloeophyllum*, such as one derived from a strain of *Gloeophyllum trabeum*, such as the one shown in SEQ ID NO: 18.
36. The enzyme composition of any of paragraphs 1-35, wherein the glucoamylase is selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.
37. The enzyme composition of paragraph 36, wherein the glucoamylase is *Gloeophyllum trabeum* glucoamylase shown in SEQ ID NO: 18 herein, preferably having one or more of the following substitutions: S95P, A121P, especially S95P+A21P.
38. The enzyme composition of paragraphs 1-37, comprising *Gloeophyllum trabeum* glucoamylase shown in SEQ ID NO: 18 herein, preferably having one or more of the following substitutions: S95P, A121P, especially S95P+A21P, and an alpha-amylase derived from a *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, preferably one having one or more of the following substitutions: G128D, D143N, especially G128D+D143N.
39. The enzyme composition of paragraphs 1-38, wherein the glucoamylase is derived from *Pycnoporus*, preferably *Pycnoporus sanguineus*, especially the one shown in SEQ ID NO: 17 herein.
40. The enzyme composition of paragraphs 1-39, wherein the enzyme composition comprises the *Pycnoporus sanguineus* glucoamylase shown in SEQ ID NO: 17 herein, and an alpha-amylase derived from a *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, preferably one having one or more of the following substitutions: G128D, D143N, especially G128D+D143N.
41. The enzyme composition of any of paragraphs 1-40, wherein the glucoamylase is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.
42. The enzyme composition of any of paragraphs 1-41, further comprising a pullulanase, such as one derived from *Bacillus* sp., such as the one shown in SEQ ID NO: 15 herein.
43. The enzyme composition of paragraph 42, wherein the pullulanase, such as *Bacillus* sp. pullulanase, is selected from the group consisting of:
(i) a pullulanase comprising the mature polypeptide of SEQ ID NO: 15 herein;
(ii) a pullulanase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 15 herein.
44. The enzyme composition of paragraphs 42 or 43, comprising a pullulanase, such as a *Bacillus deramificans* pullulanase, a *Talaromyces emersonii* glucoamylase and/or *Gloeophyllum sepiarium* glucoamylase.
45. The enzyme composition of any of paragraphs 1-44, wherein the alpha-amylase is of fungal or bacterial origin.
46. The enzyme composition of any of paragraphs 1-45, wherein the alpha-amylase is derived from a strain of the genus *Rhizomucor*, preferably a strain the *Rhizomucor pusillus*, such as the one shown in SEQ ID NO: 3 in WO 2013/006756, or the genus *Meripilus*, preferably a strain of *Meripilus giganteus*.
47. The enzyme composition of any of paragraphs 1-46, wherein the alpha-amylase is derived from a *Rhizomucor pusillus* with an *Aspergillus niger* glucoamylase linker and starch-binding domain (SBD), such as the one shown in SEQ ID NO: 13 herein, or an alpha-amylase selected from the group consisting of:
(i) an alpha-amylase comprising the mature polypeptide of SEQ ID NO: 13 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 13 herein.
48. The enzyme composition of any of paragraphs 45-48, wherein the alpha-amylase is a variant of the alpha-amylase shown in SEQ ID NO: 13 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 13 for numbering).
49. The enzyme composition of any of paragraphs 1-48, wherein the alpha-amylase is derived from a *Rhizomucor pusillus* with an *Aspergillus niger* glucoamylase linker and starch-binding domain (SBD), preferably disclosed as SEQ ID NO: 13 herein, preferably having one or more of the following substitutions: G128D, D143N, preferably G128D+D143N (using SEQ ID NO: 13 for numbering).
50. The enzyme composition of any of paragraphs 1-49, wherein the protease is of fungal origin.
51. The enzyme composition of any of paragraphs 1-50, wherein the protease is a metallo protease derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 3 herein.

52. The enzyme composition of any of paragraphs 1-51, wherein the protease, such as *Thermoascus aurantiacus* protease, is selected from the group consisting of:
(i) a protease comprising the mature polypeptide of SEQ ID NO: 3 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 3 herein.

53. The enzyme composition of any of paragraphs 1-52, wherein the protease is of bacterial origin.

54. The enzyme composition of any of paragraphs 1-53, wherein the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 5 herein.

55. The enzyme composition of any of paragraphs 1-54, wherein the protease, such as *Pyrococcus furiosus* protease, is selected from the group consisting of:
(i) a protease comprising the mature polypeptide of SEQ ID NO: 5 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 5 herein.

56. The enzyme composition of any of paragraphs 1-55, wherein the protease is derived from *Meripilus giganteus*, such as *Meripilus giganteus* protease 3 shown as SEQ ID NO: 19 herein and SEQ ID NO: 5 in WO 2014/037438.

57. The enzyme composition of any of paragraphs 1-56, wherein the protease, such as *Meripilus giganteus* protease 3, is selected from the group consisting of:
(i) a protease comprising the mature polypeptide of SEQ ID NO: 19 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

58. The enzyme composition of any of paragraphs 1-57, wherein the protease is derived from *Meripilus giganteus*, such as *Meripilus giganteus* protease 3 (peptidase family S53 protease) concerned in Example 2 in WO 2014/037438 and shown as SEQ ID NO: 20 herein.

59. The enzyme composition of any of paragraphs 1-58, wherein the protease, such as *Meripilus giganteus* protease 3, is selected from the group consisting of:
(i) a protease comprising the mature polypeptide of SEQ ID NO: 20 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

60. The enzyme composition of any of paragraphs 1-59, wherein the composition comprises
i) fungal glucoamylase;
ii) fungal alpha-amylase;
iii) cellulolytic enzyme composition derived from a strain of *Trichoderma reesei*, further comprising a GH61 polypeptide, beta-glucosidase CBH I and CBH II;
iv) optionally protease.

61. The enzyme composition of any of paragraphs 1-60, wherein the composition comprises
i) *Trametes cingulata* glucoamylase;
ii) *Rhizomucor pusillus* alpha-amylase, or variant thereof;
iii) cellulolytic enzyme composition derived from a strain of *Trichoderma reesei*, further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II; optionally
iv) protease from *Thermoascus aurantiacus*, or variant thereof.

62. The enzyme composition of any of paragraphs 1-61, wherein the composition comprises
i) *Trametes cingulata* glucoamylase;
ii) *Rhizomucor pusillus* alpha-amylase, or variant thereof,
iii) cellulolytic enzyme composition derived from a strain of *Trichoderma reesei* cellulolytic composition further comprising *Penicillium emersonii* GH61A polypeptide, *Aspergillus fumigatus* beta-glucosidase with the following substitutions: F100D, S283G, N456E, F512Y, and optionally *Aspergillus fumigatus* CBH I and *Aspergillus fumigatus* CBH II;
optionally iv) protease from Pyropoccus *furiosus*.

63. The enzyme composition of any of paragraphs 1-62, further comprising an enzyme selected from the group of trehalase and pectinase, such as pectin lyase or polygalacturonase.

64. The enzyme composition of paragraph 63, wherein the trehalase is of fungal origin, such as derived from a strain of *Trichoderma*, such as *Trichoderma reesei*, such as the one shown in SEQ ID NO: 14 herein.

65. The enzyme composition of paragraph 63 or 64, wherein the trehalase, such as *Trichoderma reesei* trehalase, is selected from the group consisting of:
(i) a trehalase comprising the mature polypeptide of SEQ ID NO: 14 herein;
(ii) a trehalase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 14 herein.

66. A process of producing a fermentation product from starch containing material, comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase and alpha-amylase; and optionally protease.

67. The process of paragraph 66, wherein the glucoamylase is *Gloeophyllum* glucoamylase, preferably *Gloeophyllum trabeum* glucoamylase.

68. The process of any of paragraphs 66 or 67, wherein the glucoamylase is the *Gloeophyllum trabeum* glucoamylase shown in SEQ ID NO: 18 or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein.

69. The process any of paragraphs 66-68, wherein the glucoamylase is the *Gloeophyllum trabeum* glucoamylase shown in SEQ ID NO: 18 having one of the following substitutions: V59A; S95P; A121P; T119W; S95P+A121P; V59A+S95P; S95P+T119W; V59A+S95P+A121P; or S95P+T119W+A121P, especially S95P+A121P.

70. The process of any of paragraphs 66-69, wherein the alpha-amylase is derived from *Rhizomucor pusillus*, preferably with an *Aspergillus niger* glucoamylase linker and starch-binding domain (SBD), preferably the one disclosed as V039 in Table 5 in WO 2006/069290 or SEQ ID NO: 13 herein.

71. The process of any of paragraphs 66-70, wherein the alpha-amylase is derived from *Rhizomucor pusillus*.

72. The process of any of paragraphs 66-71, wherein the glucoamylase is selected from the group consisting of:
(i) a glucoamylase comprising the mature polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 18 herein.

73. The process of any of paragraphs 66-72, wherein the alpha-amylase is *Rhizomucor pusillus* alpha-amylase with an *Aspergillus niger* glucoamylase linker and starch-binding domain (SBD), preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering).

74. The process any of paragraphs 66-73, wherein the glucoamylase is the *Gloeophyllum trabeum* glucoamylase shown in SEQ ID NO: 18 herein having one of the following substitutions: S95P+A121P and the alpha-amylase is is *Rhizomucor pusillus* alpha-amylase with an *Aspergillus niger* glucoamylase linker and starch-binding domain (SBD), preferably one having the following substitutions G128D+D143N (using SEQ ID NO: 13 for numbering).

75. The process of any of paragraphs 66-74, wherein the glucoamylase is the *Pycnoporus sanguineus* glucoamylase shown in SEQ ID NO: 17 herein.

76. The process of any of paragraphs 66-75, wherein the glucoamylase is selected from the group consisting of:
(i) a glucoamylase comprising the mature polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 17 herein.

77. The process of any of paragraphs 66-76, wherein the glucoamylase is the *Pycnoporus sanguineus* glucoamylase shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein, and the alpha-amylase is the *Rhizomucor pusillus* with an *Aspergillus niger* glucoamylase linker and starch-binding domain (SBD), preferably the one disclosed as V039 in Table 5 in WO 2006/069290 or SEQ ID NO: 13 herein, or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably one having one or more of the following substitutions: G128D, D143N, especially G128D+D143N.

78. The process of any of paragraphs 66-77, wherein the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

79. The process of any of paragraphs 66-78, wherein the total dose of glucoamylase and alpha-amylase added is from 10-1,000 μg/g DS, such as from 50-500 μg/g DS, such as 75-250 μg/g DS.

76. The process of any of paragraphs 66-75, wherein the total dose of cellulolytic enzyme composition added is from 10-500 μg/g DS, such as from 20-400 μg/g DS, such as 20-300 μg/g DS.

77. The process of any of paragraphs 66-77, wherein the dose of protease added is from 1-200 μg/g DS, such as from 2-100 μg/g DS, such as 3-50 μg/g DS.

78. The process of any of paragraphs 66-77, wherein the protease is derived from *Meripilus giganteus*, such as *Meripilus giganteus* protease 3 shown as SEQ ID NO: 19 herein and SEQ ID NO: 5 in WO 2014/037438.

79. The process of any of paragraphs 66-78, wherein the protease, such as *Meripilus giganteus* protease 3, is selected from the group consisting of:
(i) a protease comprising the mature polypeptide of SEQ ID NO: 19 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 19 herein.

80. The process of any of paragraphs 66-79, wherein the protease is derived from *Meripilus giganteus*, such as *Meripilus giganteus* protease 3 (peptidase family S53 protease) concerned in Example 2 in WO 2014/037438 and shown as SEQ ID NO: 20 herein.

81. The process of any of paragraphs 66-80, wherein the protease, such as *Meripilus giganteus* protease 3, is selected from the group consisting of:
(i) a protease comprising the mature polypeptide of SEQ ID NO: 20 herein;
(ii) a protease comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the mature polypeptide of SEQ ID NO: 20 herein.

82. A process of producing of any of paragraphs 66-81, comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase;
  ii) alpha-amylase;
  iii) cellulolytic enzyme composition;
  optionally iv) protease.

83. The process of any of paragraphs 66-82, wherein an enzyme composition of any of paragraphs 1-81 are added or present during saccharification and/or fermentation.

84. The process of any of claims 66-83, wherein saccharification and fermentation are done separately or simultaneously (i.e., as a one-step process or no-cook process).

85. The process of any of paragraphs 66-85, wherein the fermentation product, such as ethanol, is recovered after fermentation.

86. The process of any of paragraphs 66-85, wherein the starch-containing material is plant material selected from the corn (maize), cobs, wheat, barley, rye, milo, sago, cassava, tapioca, sorghum, rice, peas, beans, sweet potatoes, or a mixture thereof, preferably corn.

87. The process of any of paragraphs 66-86, wherein the starch-containing material is granular starch.

88. The process of any of paragraphs 66-87, wherein the process is carried out at a pH in the range between 3 and 7, preferably from 3 to 6, or more preferably from 3.5 to 5.0.

89. The process of any of paragraphs 66-88, wherein the dry solid content (DS) lies in the range from 10-55 wt.-% (DS), preferably 25-45 wt.-%, more preferably 30-40% of starch-containing material.

90. The process of any of paragraphs 66-89, wherein the sugar concentration is kept at a level below about 6 wt.-%, preferably 3 wt.-%, during saccharification and fermentation, especially below 0.25 wt.-%.

91. The process of any of paragraphs 66-90, wherein a slurry comprising starch-containing material reduced in particle size and water, is prepared before step (a).

92. The process of any of paragraphs 66-91, wherein the starch-containing material is prepared by reducing the particle size of the starch-containing material, preferably by milling, such that at least 50% of the starch-containing material has a particle size of 0.1-0.5 mm.

93. The process of any of paragraphs 66-92, wherein the starch-containing plant material is reduced in particle size, such by dry or wet milling or using particle size emulsion technology.

94. The process of any of paragraphs 66-93, wherein the fermentation is carried out for 30 to 150 hours, preferably 48 to 96 hours.

95. The process of any of paragraphs 66-94, wherein the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

96. The process of any of paragraphs 66-95, wherein further a protease is present during saccharification and/or fermentation.

97. The process of any of paragraphs 66-96, wherein the glucoamylase is present and/or added in an amount of 0.001 to 10 AGU/g DS, preferably from 0.01 to 5 AGU/g DS, especially 0.1 to 0.5 AGU/g DS.

98. The process of any of paragraphs 66-97, wherein the glucoamylase is present and/or added in an amount of 10-1,000 micro grams Enzyme Protein/g DS 99. The process of any of paragraphs 66-98, wherein the alpha-amylase is present and/or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

100. The process of any of paragraphs 66-99, wherein the alpha-amylase is present and/or added in an amount of 10-1,000 micro grams Enzyme Protein/g DS.

101. The process of any of paragraphs 66-100, wherein the cellulolytic enzyme composition is present and/or added in an amount 1-10,000 micrograms EP/g DS, such as 2-5,000, such as 3 and 1,000, such as 4 and 500 micrograms EP/g DS.

102. The process of any of paragraphs 66-101, wherein cellulolytic enzyme composition is present and/or added in an amount in the range from 0.1-100 FPU per gram total solids (TS), preferably 0.5-50 FPU per gram TS, especially 1-20 FPU per gram TS.

103. The process of any of paragraphs 66-102, wherein protease is present and/or added in an amount in the range 1-1,000 µg EP/g DS, such as 2-500 µg EP/g DS, such as 3-250 µg EP/g DS.

104. The process of any of paragraphs 66-104, wherein the fermentation organism is yeast, such as yeast derived from a strain of the genus *Saccharomyces*, preferably a strain of *Saccharomyces cerevisiae*.

105. The process of any of paragraphs 66-104, wherein the fermenting organism is added to the fermentation, such as yeast, so that the count per mL of fermentation medium is in the range from $10^5$ to $10^{12}$, preferably from $10^7$ to $10^{10}$, especially about $5 \times 10^7$.

106. The process of any of paragraphs 66-105, comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Trametes cingulata*;
  ii) alpha-amylase derived from *Rhizomucor pusillus* with an *Aspergillus niger* glucoamylase linker and starch-binding domain (SBD), or a variant thereof.

107. The process of any of paragraphs 66-106, comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Trametes cingulata*;
  ii) alpha-amylase derived from *Rhizomucor pusillus* with an *Aspergillus niger* glucoamylase linker and starch-binding domain (SBD), or a variant thereof;
  iii) cellulolytic enzyme composition derived from a strain of *Trichoderma reesei*;
  optionally iv) a protease from *Thermoascus aurantiacus*, or a variant thereof and/or *Pyrococcus furiosus*, or *Meripilus giganteus*.

108. The process of any of paragraphs 66-107, comprising:
(a) saccharifying a starch-containing material at a temperature below the initial gelatinization temperature; and
(b) fermenting using a fermentation organism;
wherein saccharification and/or fermentation is done in the presence of the following enzymes:
  i) glucoamylase derived from *Gloeophyllum trabeum* shown in SEQ ID NO: 18 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, preferably having at least one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 for numbering);

ii) alpha-amylase derived from *Rhizomucor pusillus* with an *Aspergillus niger* glucoamylase linker and starch-binding domain (SBD), or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18 herein, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering).

109. The process of any of paragraphs 66-108, comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase derived from *Gloeophyllum trabeum* shown in SEQ ID NO: 18, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 18, preferably having at least one of the following substitutions: V59A; S95P; A121P; T119W; S95P+A121P; V59A+S95P; S95P+T119W; V59A+S95P+A121P; or S95P+T119W+A121P, especially S95P+A121P (using SEQ ID NO: 18 for numbering);

ii) alpha-amylase derived from *Rhizomucor pusillus* with an *Aspergillus niger* glucoamylase linker and starch-binding domain (SBD), preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering);

iii) cellulolytic enzyme composition derived from a strain of *Trichoderma reesei*; preferably a cellulolytic enzyme composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a variant thereof, preferably a variant having one of, preferably all of, the following substitutions: F100D, S283G, N456E, F512Y and optionally *Aspergillus fumigatus* Cel7A CBH1 disclosed as SEQ ID NO: 6 in WO2011/057140 and SEQ ID NO: 6 herein and *Aspergillus fumigatus* CBH II disclosed as SEQ ID NO: 18 in WO 2011/057140 and as SEQ ID NO: 7 herein;

optionally iv) a protease from *Thermoascus aurantiacus*, or a variant thereof and/or *Pyrococcus furiosus*, or *Meripilus giganteus*.

110. The process of any of paragraphs 66-109, comprising:
(i) saccharifying a starch-containing material at a temperature below the initial gelatinization temperature; and
(ii) fermenting using a fermentation organism;
wherein saccharification and/or fermentation is done in the presence of the following enzymes:
i) glucoamylase derived from *Pycnoporus sanguineus* shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein;

ii) alpha-amylase derived from *Rhizomucor pusillus* with an *Aspergillus niger* glucoamylase linker and starch-binding domain (SBD), or an alpha-amylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 13 herein, preferably one having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C, especially G128D+D143N (using SEQ ID NO: 13 for numbering);

iii) cellulolytic enzyme composition derived from a strain of *Trichoderma reesei*;
preferably a cellulolytic composition derived from *Trichoderma reesei* further comprising *Penicillium emersonii* GH61A polypeptide disclosed as SEQ ID NO: 2 in WO 2011/041397 or SEQ ID NO: 10 herein, and *Aspergillus fumigatus* beta-glucosidase disclosed as SEQ ID NO: 2 in WO 2005/047499 or SEQ ID NO: 8 herein, or a beta-glucosidase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 8 herein, or a variant thereof, preferably a variant having one of, preferably all of, the following substitutions: F100D, S283G, N456E, F512Y (using SEQ ID NO: 8 for numbering) and optionally *Aspergillus fumigatus* Cel7A CBH1 disclosed as SEQ ID NO: 6 in WO2011/057140 and SEQ ID NO: 6 herein and *Aspergillus fumigatus*

CBH II disclosed as SEQ ID NO: 18 in WO 2011/057140 and as SEQ ID NO: 7 herein.
  optionally iv) a protease from *Thermoascus aurantiacus*, or a variant thereof and/or *Pyrococcus furiosus*, or *Meripilus giganteus*.
111. The process of any of paragraphs 66-110, comprising:
(i) saccharifying a starch-containing material at a temperature below the initial gelatinization temperature; and
(ii) fermenting using a fermentation organism;
wherein saccharification and/or fermentation is done in the presence of the following enzymes:
  i) glucoamylase derived from *Pycnoporus sanguineus* shown in SEQ ID NO: 17 herein, or a glucoamylase having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 17 herein;
  ii) alpha-amylase derived from *Rhizomucor pusillus* with an *Aspergillus niger* glucoamylase linker and starch-binding domain (SBD), having the following substitutions G128D+D143N (using SEQ ID NO: 13 herein for numbering);
  iii) optionally cellulolytic enzyme composition derived from a strain of *Trichoderma reesei*;
  iv) a *Meripilus giganteus* protease 3, preferably the one shown in SEQ ID NO: 20, or a protease having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to SEQ ID NO: 20.

112. The process of any of paragraphs 66-111, wherein the ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

113. The process of paragraphs 66-112, wherein the saccharification and fermentation are carried out simultaneously.

114. The process of any of paragraphs 66-113, wherein an enzyme composition of paragraphs 1-65 is used as the enzymes/enzyme composition in saccharification or fermentation or simultaneous saccharification and fermentation.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

The invention claimed is:

1. An enzyme composition comprising:
(i) a glucoamylase, wherein the glucoamylase is selected from the group consisting of:
   (a) a glucoamylase comprising an amino acid sequence having at least 85% identity to the amino acid sequence of SEQ ID NO: 4; and
   (b) a glucoamylase comprising an amino acid sequence having at least 85% identity to the amino acid sequence of SEQ ID NO: 18;
(ii) an alpha-amylase, wherein the alpha-amylase is derived from a *Rhizomucor pusillus* with an *Aspergillus niger* glucoamylase linker and starch-binding domain (SBD); and
(iii) optionally a protease.

2. The enzyme composition of claim 1 further comprising a cellulolytic enzyme composition.

3. The enzyme composition of claim 2, wherein the cellulolytic enzyme composition is derived from a strain of *Trichoderma*, a strain of *Humicola*, a strain of *Chrysosporium*, or a strain of *Penicillium*.

4. The enzyme composition of claim 1, wherein the glucoamylase
comprises or consists of the amino acid sequence of SEQ ID NO: 4.

5. The enzyme composition of claim 1, wherein the glucoamylase
comprises or consists of the amino acid sequence of SEQ ID NO: 18.

6. The enzyme composition of claim 5, wherein the glucoamylase is *Gloeophyllum trabeum* glucoamylase shown in SEQ ID NO: 18 having one or more of the following substitutions: S95P, A121P, or S95P+A121P.

7. The enzyme composition of claim 1, comprising the *Gloeophyllum trabeum* glucoamylase shown in SEQ ID NO: 18 having one or more of the following substitutions: S95P, A121P, or S95P+A121P, and the *Rhizomucor pusillus* alpha-amylase with an *Aspergillus niger* glucoamylase linker and starch-binding domain (SBD) disclosed as SEQ ID NO: 13, and having one or more of the following substitutions: G128D, D143N, or G128D+D143N.

8. The enzyme composition of claim 1, wherein the alpha-amylase is the one shown in SEQ ID NO: 13, or an alpha-amylase selected from the group consisting of:
(i) an alpha-amylase comprising the amino acid sequence of SEQ ID NO: 13; and
(ii) an alpha-amylase comprising an amino acid sequence having at least 85%, at least 90%, at least 91%, at least 92%, at least 93%, at least 94%, at least 95%, at least 96%, at least 97%, at least 98%, or at least 99% identity to the amino acid sequence of SEQ ID NO: 13.

9. The enzyme composition of claim 8, wherein the alpha-amylase is a variant of the alpha-amylase shown in SEQ ID NO: 13 having at least one of the following substitutions or combinations of substitutions: D165M; Y141W; Y141R; K136F; K192R; P224A;
P224R; S123H+Y141W; G20S+Y141W; A76G+Y141W; G128D+Y141W; G128D+D143N;
P219Q+Y141W; N142D+D143N; Y141W+K192R; Y141W+D143N; Y141W+N383R; Y141W +P219C+ A265C; Y141W+N142D+D143N; Y141W+K192R V410A; G128D+Y141W+D143N; Y141W+D143N+ P219C; Y141W+D143N+K192R; G128D+D143N+ K192R;
Y141W+D143N+K192R+P219C; G128D+Y141W+ D143N+K192R; or G128D+Y141W+D143N+ K192R+P219C (using SEQ ID NO: 13 for numbering).

10. The enzyme composition of claim 1, further comprising an enzyme selected from the group of trehalase and pectinase.

11. A process of producing a fermentation product from starch-containing material, comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase and alpha-amylase; and optionally protease, wherein the glucoamylase is selected from the group consisting of:
   (a) a glucoamylase comprising an amino acid sequence having at least 85% identity to the amino acid sequence of SEQ ID NO: 4; and
   (b) a glucoamylase comprising an amino acid sequence having at least 85% identity to the amino acid sequence of SEQ ID NO: 18; and
wherein the alpha-amylase is derived from a *Rhizomucor pusillus* with an *Aspergillus niqer* glucoamylase linker and starch-binding domain (SBD).

12. The process of claim 11, wherein the glucoamylase is the *Gloeophyllum trabeum* glucoamylase shown in SEQ ID NO: 18 having one of the following substitutions: S95P+ A121P and the alpha-amylase is the *Rhizomucor pusillus* alpha-amylase with an *Aspergillus niger* glucoamylase linker and starch-binding domain (SBD).

13. The process of claim 11, further wherein saccharification and/or fermentation is done in the presence of a cellulolytic enzyme composition derived from a strain selected from the group consisting of *Trichoderma, Humicola, Chrysosporium,* and *Penicillium*.

14. The process of claim 11, comprising:
   (a) saccharifying a starch-containing material at a temperature below the initial gelatinization temperature; and
   (b) fermenting using a fermentation organism;
   wherein saccharification and/or fermentation is done in the presence of the following enzymes:
      i) glucoamylase derived from the *Gloeophyllum trabeum* amino acid sequence shown in SEQ ID NO: 18, or a glucoamylase having at least 85%, at least 90%, at least 91%, at least 92%, at least 93%, at least 94%, at least 95%, at least 96%, at least 97%, at least 98%, or at least 99% identity to the amino acid sequence of SEQ ID NO: 18;
      ii) alpha-amylase derived from *Rhizomucor pusillus* with an *Aspergillus niger* glucoamylase linker and starch-binding domain (SBD) shown in SEQ ID NO: 13, or an alpha-amylase having at least 85%, at least 90%, at least 91%, at least 92%, at least 93%, at least 94%, at least 95%, at least 96%, at least 97%, at least 98%, or at least 99% identity to SEQ ID NO: 13.

15. The process of claim 11, wherein the ratio between glucoamylase and alpha-amylase is between 99:1 and 1:2 (mg EP glucoamylase: mg EP alpha-amylase).

* * * * *

UNITED STATES PATENT AND TRADEMARK OFFICE
CERTIFICATE OF CORRECTION

| | | |
|---|---|---|
| PATENT NO. | : 11,155,798 B2 | Page 1 of 1 |
| APPLICATION NO. | : 16/567167 | |
| DATED | : October 26, 2021 | |
| INVENTOR(S) | : Jump et al. | |

It is certified that error appears in the above-identified patent and that said Letters Patent is hereby corrected as shown below:

In the Claims

Please amend Claim 9 (Column 116, Lines 19-35) as follows:
9. The enzyme composition of claim 8, wherein the alpha-amylase is a variant of the alpha-amylase shown in SEQ ID NO: 13 having at least one of the following substitutions or combinations of substitutions: D165M; Y141W; Y141R; K136F; K192R; P224A; P224R; S123H + Y141W; G20S + Y141W; A76G + Y141W; G128D + Y141W; G128D + D143N; <u>P219C</u> + Y141W; N142D + D143N; Y141W+ K192R; Y141W+ D143N; Y141W + N383R; Y141W+ P219C + A265C; Y141W+ N142D + D143N; Y141W + K192R + V410A; G128D + Y141W + D143N; Y141W+ D143N + P219C; Y141W+ D143N + K192R; G128D + D143N + K192R; Y141W+ D143N + K192R + P219C; G128D + Y141W+ D143N + K192R; or G128D + Y141W + D143N + K192R + P219C (using SEQ ID NO: 13 for numbering).

Signed and Sealed this
Twenty-seventh Day of June, 2023

Katherine Kelly Vidal
*Director of the United States Patent and Trademark Office*

SEQUENCE LISTING

```
<160> NUMBER OF SEQ ID NOS: 20

<210> SEQ ID NO 1
<211> LENGTH: 515
<212> TYPE: PRT
<213> ORGANISM: Bacillus stearothermophilus
<220> FEATURE:
<221> NAME/KEY: mat_peptide
<222> LOCATION: (1)..(515)

<400> SEQUENCE: 1

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160
```

```
Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 2
<211> LENGTH: 1068
<212> TYPE: DNA
<213> ORGANISM: Thermoascus aurantiacus
<220> FEATURE:
<221> NAME/KEY: CDS
<222> LOCATION: (1)..(1065)
<220> FEATURE:
```

```
<221> NAME/KEY: misc_signal
<222> LOCATION: (1)..(57)
<220> FEATURE:
<221> NAME/KEY: misc_feature
<222> LOCATION: (58)..(534)
<220> FEATURE:
<221> NAME/KEY: mat_peptide
<222> LOCATION: (535)..(1068)

<400> SEQUENCE: 2
```

| | | | | | | | | | | | | | | | |
|---|---|---|---|---|---|---|---|---|---|---|---|---|---|---|---|
| atg | cgg | ctc | gtt | gct | tcc | cta | acg | gcc | ttg | gtg | gcc | ttg | tcc | gta | 45 |
| Met | Arg | Leu | Val | Ala | Ser | Leu | Thr | Ala | Leu | Val | Ala | Leu | Ser | Val | |
| | -175 | | | | -170 | | | | -165 | | | | | | |

```
cct gtc ttt ccc gct gct gtc aac gtg aag cgt gct tcg tcc tac      90
Pro Val Phe Pro Ala Ala Val Asn Val Lys Arg Ala Ser Ser Tyr
        -160                -155                -150 ctg gag atc act ctg agc cag gtc agc aac act ctg atc aag gcc     135
Leu Glu Ile Thr Leu Ser Gln Val Ser Asn Thr Leu Ile Lys Ala
        -145                -140                -135 gtg gtc cag aac act ggt agc gac gag ttg tcc ttc gtt cac ctg     180
Val Val Gln Asn Thr Gly Ser Asp Glu Leu Ser Phe Val His Leu
        -130                -125                -120 aac ttc ttc aag gac ccc gct cct gtc aaa aag gta tcg gtc tat     225
Asn Phe Phe Lys Asp Pro Ala Pro Val Lys Lys Val Ser Val Tyr
        -115                -110                -105 cgc gat ggg tct gaa gtg cag ttc gag ggc att ttg agc cgc tac aaa 273
Arg Asp Gly Ser Glu Val Gln Phe Glu Gly Ile Leu Ser Arg Tyr Lys
        -100                -95                 -90 tcg act ggc ctc tct cgt gac gcc ttt act tat ctg gct ccc gga gag 321
Ser Thr Gly Leu Ser Arg Asp Ala Phe Thr Tyr Leu Ala Pro Gly Glu
         -85                -80                 -75 tcc gtc gag gac gtt ttt gat att gct tcg act tac gat ctg acc agc 369
Ser Val Glu Asp Val Phe Asp Ile Ala Ser Thr Tyr Asp Leu Thr Ser
         -70                -65                 -60 ggc ggc cct gta act atc cgt act gag gga gtt gtt ccc tac gcc acg 417
Gly Gly Pro Val Thr Ile Arg Thr Glu Gly Val Val Pro Tyr Ala Thr
-55                 -50                 -45                 -40 gct aac agc act gat att gcc ggc tac atc tca tac tcg tct aat gtg 465
Ala Asn Ser Thr Asp Ile Ala Gly Tyr Ile Ser Tyr Ser Ser Asn Val
                -35                 -30                 -25 ttg acc att gat gtc gat ggc gcc gct gct gcc act gtc tcc aag gca 513
Leu Thr Ile Asp Val Asp Gly Ala Ala Ala Ala Thr Val Ser Lys Ala
        -20                 -15                 -10 atc act cct ttg gac cgc cgc act agg atc agt tcc tgc tcc ggc agc 561
Ile Thr Pro Leu Asp Arg Arg Thr Arg Ile Ser Ser Cys Ser Gly Ser
         -5                 -1   1                5 aga cag agc gct ctt act acg gct ctc aga aac gct gct tct ctt gcc 609
Arg Gln Ser Ala Leu Thr Thr Ala Leu Arg Asn Ala Ala Ser Leu Ala
 10                 15                 20                 25 aac gca gct gcc gac gcg gct cag tct gga tca gct tca aag ttc agc 657
Asn Ala Ala Ala Asp Ala Ala Gln Ser Gly Ser Ala Ser Lys Phe Ser
                 30                 35                 40 gag tac ttc aag act act tct agc tct acc cgc cag acc gtg gct gcg 705
Glu Tyr Phe Lys Thr Thr Ser Ser Ser Thr Arg Gln Thr Val Ala Ala
                 45                 50                 55 cgt ctt cgg gct gtt gcg cgg gag gca tct tcg tct tct tcg gga gcc 753
Arg Leu Arg Ala Val Ala Arg Glu Ala Ser Ser Ser Ser Ser Gly Ala
 60                 65                 70 acc acg tac tac tgc gac gat ccc tac ggc tac tgt tcc tcc aac gtc 801
Thr Thr Tyr Tyr Cys Asp Asp Pro Tyr Gly Tyr Cys Ser Ser Asn Val
 75                 80                 85
```

```
ctg gct tac acc ctg cct tca tac aac ata atc gcc aac tgt gac att    849
Leu Ala Tyr Thr Leu Pro Ser Tyr Asn Ile Ile Ala Asn Cys Asp Ile
 90              95                 100                 105 ttc tat act tac ctg ccg gct ctg acc agt acc tgt cac gct cag gat    897
Phe Tyr Thr Tyr Leu Pro Ala Leu Thr Ser Thr Cys His Ala Gln Asp
             110                 115                 120 caa gcg acc act gcc ctt cac gag ttc acc cat gcg cct ggc gtc tac    945
Gln Ala Thr Thr Ala Leu His Glu Phe Thr His Ala Pro Gly Val Tyr
             125                 130                 135 agc cct ggc acg gac gac ctg gcg tat ggc tac cag gct gcg atg ggt    993
Ser Pro Gly Thr Asp Asp Leu Ala Tyr Gly Tyr Gln Ala Ala Met Gly
             140                 145                 150 ctc agc agc agc cag gct gtc atg aac gct gac acc tac gct ctc tat   1041
Leu Ser Ser Ser Gln Ala Val Met Asn Ala Asp Thr Tyr Ala Leu Tyr
             155                 160                 165 gcg aat gcc ata tac ctt ggt tgc taa                                1068
Ala Asn Ala Ile Tyr Leu Gly Cys
170                 175

<210> SEQ ID NO 3
<211> LENGTH: 355
<212> TYPE: PRT
<213> ORGANISM: Thermoascus aurantiacus

<400> SEQUENCE: 3

Met Arg Leu Val  Ala Ser Leu Thr  Ala Leu Val Ala  Leu Ser Val
    -175                 -170                 -165

Pro Val Phe Pro  Ala Ala Val Asn  Val Lys Arg Ala  Ser Ser Tyr
    -160                 -155                 -150

Leu Glu Ile Thr  Leu Ser Gln Val  Ser Asn Thr Leu  Ile Lys Ala
    -145                 -140                 -135

Val Val Gln Asn  Thr Gly Ser Asp  Glu Leu Ser Phe  Val His Leu
    -130                 -125                 -120

Asn Phe Phe Lys  Asp Pro Ala Pro  Val Lys Lys Val  Ser Val Tyr
    -115                 -110                 -105

Arg Asp Gly Ser  Glu Val Gln Phe  Glu Gly Ile Leu  Ser Arg Tyr Lys
        -100                 -95                  -90

Ser Thr Gly Leu  Ser Arg Asp Ala  Phe Thr Tyr Leu  Ala Pro Gly Glu
         -85                  -80                  -75

Ser Val Glu Asp  Val Phe Asp Ile  Ala Ser Thr Tyr  Asp Leu Thr Ser
         -70                  -65                  -60

Gly Gly Pro Val  Thr Ile Arg Thr  Glu Gly Val Val  Pro Tyr Ala Thr
-55                  -50                  -45                  -40

Ala Asn Ser Thr  Asp Ile Ala Gly  Tyr Ile Ser Tyr  Ser Ser Asn Val
                 -35                  -30                  -25

Leu Thr Ile Asp  Val Asp Gly Ala  Ala Ala Thr Val  Ser Lys Ala
                 -20                  -15                  -10

Ile Thr Pro Leu  Asp Arg Arg Thr  Arg Ile Ser Ser  Cys Ser Gly Ser
         -5                   -1    1                   5

Arg Gln Ser Ala  Leu Thr Thr Ala  Leu Arg Asn Ala  Ala Ser Leu Ala
10                   15                   20                   25

Asn Ala Ala Asp  Ala Ala Gln Ser  Gly Ser Ala Ser  Lys Phe Ser
                 30                   35                   40

Glu Tyr Phe Lys  Thr Thr Ser Ser  Ser Thr Arg Gln  Thr Val Ala Ala
                 45                   50                   55

Arg Leu Arg Ala  Val Ala Arg Glu  Ala Ser Ser Ser  Ser Ser Gly Ala
60                   65                   70
```

```
Thr Thr Tyr Tyr Cys Asp Asp Pro Tyr Gly Tyr Cys Ser Ser Asn Val
 75                  80                  85

Leu Ala Tyr Thr Leu Pro Ser Tyr Asn Ile Ile Ala Asn Cys Asp Ile
 90                  95                 100                 105

Phe Tyr Thr Tyr Leu Pro Ala Leu Thr Ser Thr Cys His Ala Gln Asp
                110                 115                 120

Gln Ala Thr Thr Ala Leu His Glu Phe Thr His Ala Pro Gly Val Tyr
            125                 130                 135

Ser Pro Gly Thr Asp Asp Leu Ala Tyr Gly Tyr Gln Ala Ala Met Gly
        140                 145                 150

Leu Ser Ser Ser Gln Ala Val Met Asn Ala Asp Thr Tyr Ala Leu Tyr
155                 160                 165

Ala Asn Ala Ile Tyr Leu Gly Cys
170                 175

<210> SEQ ID NO 4
<211> LENGTH: 573
<212> TYPE: PRT
<213> ORGANISM: Gloeophyllum sepiarium

<400> SEQUENCE: 4

Met Tyr Arg Phe Leu Val Cys Ala Leu Gly Leu Ala Ala Ser Val Leu
 1               5                  10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
 50                  55                  60

Tyr Trp Tyr Thr Trp Thr Arg Asp Ser Ser Leu Val Phe Lys Ser Leu
 65                  70                  75                  80

Ile Asp Gln Tyr Thr Thr Gly Ile Asp Ser Thr Ser Ser Leu Arg Thr
                 85                  90                  95

Leu Ile Asp Asp Phe Val Thr Ala Glu Ala Asn Leu Gln Gln Val Ser
                100                 105                 110

Asn Pro Ser Gly Thr Leu Thr Thr Gly Gly Leu Gly Glu Pro Lys Phe
            115                 120                 125

Asn Val Asp Glu Thr Ala Phe Thr Gly Ala Trp Gly Arg Pro Gln Arg
        130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
                180                 185                 190

Thr Tyr Asp Leu Trp Glu Glu Val Asp Ser Ser Ser Phe Phe Thr Thr
            195                 200                 205

Ala Val Gln His Arg Ala Leu Arg Glu Gly Ala Ala Phe Ala Thr Ala
        210                 215                 220

Ile Gly Gln Thr Ser Gln Val Ser Ser Tyr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
```

```
            260                 265                 270
Leu Ala Ser Ile His Thr Tyr Asp Pro Ser Ala Gly Cys Asp Ala Ala
            275                 280                 285

Thr Phe Gln Pro Cys Ser Asp Lys Ala Leu Ser Asn Leu Lys Val Tyr
        290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335

Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
            370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 5
<211> LENGTH: 412
<212> TYPE: PRT
<213> ORGANISM: Pyrococcus furiosus
<220> FEATURE:
<221> NAME/KEY: mat_peptide
<222> LOCATION: (1)..(412)
<223> OTHER INFORMATION: Pyrococcus furiosus protease (Pfu)

<400> SEQUENCE: 5

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45
```

```
Ile Gly Trp Val Asp Phe Val Asn Gly Arg Ser Tyr Pro Tyr Asp Asp
 50                  55                  60

His Gly His Gly Thr His Val Ala Ser Ile Ala Ala Gly Thr Gly Ala
 65                  70                  75                  80

Ala Ser Asn Gly Lys Tyr Lys Gly Met Ala Pro Gly Ala Lys Leu Ala
                 85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Arg Gly Pro Thr Ala Asp Gly
        195                 200                 205

Arg Leu Lys Pro Glu Val Val Ala Pro Gly Asn Trp Ile Ile Ala Ala
210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410
```

<210> SEQ ID NO 6
<211> LENGTH: 532
<212> TYPE: PRT
<213> ORGANISM: Aspergillus fumigatus

<400> SEQUENCE: 6

Met Leu Ala Ser Thr Phe Ser Tyr Arg Met Tyr Lys Thr Ala Leu Ile

-continued

```
1               5                   10                  15
Leu Ala Ala Leu Leu Gly Ser Gly Gln Ala Gln Gln Val Gly Thr Ser
                20                  25                  30

Gln Ala Glu Val His Pro Ser Met Thr Trp Gln Ser Cys Thr Ala Gly
                35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
                100                 105                 110

Ser Gly Asn Ser Leu Arg Leu Asn Phe Val Thr Thr Ser Gln Gln Lys
                115                 120                 125

Asn Ile Gly Ser Arg Leu Tyr Met Met Lys Asp Asp Ser Thr Tyr Glu
                130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
                180                 185                 190

Tyr Gly Thr Gly Tyr Cys Asp Ser Gln Cys Pro Arg Asp Leu Lys Phe
                195                 200                 205

Ile Asn Gly Gln Ala Asn Val Glu Gly Trp Gln Pro Ser Ser Asn Asp
                210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
                260                 265                 270

Tyr Ser Ser Asp Arg Tyr Gly Gly Thr Cys Asp Pro Asp Gly Cys Asp
                275                 280                 285

Phe Asn Ser Phe Arg Gln Gly Asn Lys Thr Phe Tyr Gly Pro Gly Met
                290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
                340                 345                 350

Val Ser Gly Asn Ser Ile Thr Thr Glu Tyr Cys Thr Ala Gln Lys Ser
                355                 360                 365

Leu Phe Gln Asp Gln Asn Val Phe Glu Lys His Gly Gly Leu Glu Gly
                370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415

Thr Ala Ser Ser Thr Thr Pro Gly Val Ala Arg Gly Thr Cys Asp Ile
                420                 425                 430
```

```
Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
        450                 455                 460

Ser Gly Ser Asn Pro Gly Gly Thr Thr Thr Thr Thr Thr
465                 470                 475                 480

Gln Pro Thr Thr Thr Thr Thr Ala Gly Asn Pro Gly Thr Gly
                    485                 490                 495

Val Ala Gln His Tyr Gly Gln Cys Gly Gly Ile Gly Trp Thr Gly Pro
                500                 505                 510

Thr Thr Cys Ala Ser Pro Tyr Thr Cys Gln Lys Leu Asn Asp Tyr Tyr
                515                 520                 525

Ser Gln Cys Leu
    530
```

<210> SEQ ID NO 7
<211> LENGTH: 454
<212> TYPE: PRT
<213> ORGANISM: Aspergillus fumigatus

<400> SEQUENCE: 7

```
Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
    50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
    130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
    210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
```

```
            260                 265                 270
Ala Gly His Ala Gly Trp Leu Gly Trp Pro Ala Asn Leu Gly Pro Ala
                275                 280                 285

Ala Thr Leu Phe Ala Lys Val Tyr Thr Asp Ala Gly Ser Pro Ala Ala
            290                 295                 300

Val Arg Gly Leu Ala Thr Asn Val Ala Asn Tyr Asn Ala Trp Ser Leu
305                 310                 315                 320

Ser Thr Cys Pro Ser Tyr Thr Gln Gly Asp Pro Asn Cys Asp Glu Lys
                325                 330                 335

Lys Tyr Ile Asn Ala Met Ala Pro Leu Leu Lys Glu Ala Gly Phe Asp
            340                 345                 350

Ala His Phe Ile Met Asp Thr Ser Arg Asn Gly Val Gln Pro Thr Lys
            355                 360                 365

Gln Asn Ala Trp Gly Asp Trp Cys Asn Val Ile Gly Thr Gly Phe Gly
            370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
            435                 440                 445

Asn Ala Asn Pro Ser Phe
            450

<210> SEQ ID NO 8
<211> LENGTH: 863
<212> TYPE: PRT
<213> ORGANISM: Aspergillus fumigatus

<400> SEQUENCE: 8

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
            130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175
```

```
Ile Lys Gly Ile Gln Asp Ala Gly Val Ile Ala Thr Ala Lys His Tyr
            180                 185                 190
Ile Leu Asn Glu Gln Glu His Phe Arg Gln Val Gly Glu Ala Gln Gly
        195                 200                 205
Tyr Gly Tyr Asn Ile Thr Glu Thr Ile Ser Ser Asn Val Asp Asp Lys
    210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
            260                 265                 270
Gly Phe Gln Gly Phe Val Met Ser Asp Trp Ser Ala His His Ser Gly
        275                 280                 285
Val Gly Ala Ala Leu Ala Gly Leu Asp Met Ser Met Pro Gly Asp Ile
    290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
            340                 345                 350
Pro Pro Asn Phe Ser Ser Trp Thr Arg Asp Glu Tyr Gly Trp Glu His
        355                 360                 365
Ser Ala Val Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
            420                 425                 430
Ala Asn Gly Cys Pro Asp Arg Gly Cys Asp Asn Gly Thr Leu Ala Met
        435                 440                 445
Ala Trp Gly Ser Gly Thr Ala Asn Phe Pro Tyr Leu Val Thr Pro Glu
    450                 455                 460
Gln Ala Ile Gln Arg Glu Val Ile Ser Asn Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Phe
            500                 505                 510
Ile Ser Val Asp Gly Asn Glu Gly Asp Arg Lys Asn Leu Thr Leu Trp
        515                 520                 525
Lys Asn Gly Glu Ala Val Ile Asp Thr Val Ser His Cys Asn Asn
530                 535                 540
Thr Ile Val Val Ile His Ser Val Gly Pro Val Leu Ile Asp Arg Trp
545                 550                 555                 560
Tyr Asp Asn Pro Asn Val Thr Ala Ile Ile Trp Ala Gly Leu Pro Gly
                565                 570                 575
Gln Glu Ser Gly Asn Ser Leu Val Asp Val Leu Tyr Gly Arg Val Asn
            580                 585                 590
Pro Ser Ala Lys Thr Pro Phe Thr Trp Gly Lys Thr Arg Glu Ser Tyr
```

595                 600                 605
Gly Ala Pro Leu Leu Thr Glu Pro Asn Asn Gly Asn Gly Ala Pro Gln
            610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
675                 680                 685

Gly Glu Ile Gly Ser Ala Ala Asp Tyr Leu Tyr Pro Glu Gly Leu Lys
            690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
            755                 760                 765

Ser Ala Thr Ile Thr Asn Thr Gly Asn Val Ala Gly Tyr Glu Val Pro
770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
            835                 840                 845

Ser Ser Arg Lys Leu Pro Leu Arg Ala Pro Leu Pro Arg Val Tyr
850                 855                 860

<210> SEQ ID NO 9
<211> LENGTH: 250
<212> TYPE: PRT
<213> ORGANISM: Thermoascus aurantiacus
<220> FEATURE:
<221> NAME/KEY: SIGNAL
<222> LOCATION: (1)..(22)

<400> SEQUENCE: 9

Met Ser Phe Ser Lys Ile Ile Ala Thr Ala Gly Val Leu Ala Ser Ala
1               5                   10                  15

Ser Leu Val Ala Gly His Gly Phe Val Gln Asn Ile Val Ile Asp Gly
            20                  25                  30

Lys Lys Tyr Tyr Gly Gly Tyr Leu Val Asn Gln Tyr Pro Tyr Met Ser
        35                  40                  45

Asn Pro Pro Glu Val Ile Ala Trp Ser Thr Thr Ala Thr Asp Leu Gly
    50                  55                  60

Phe Val Asp Gly Thr Gly Tyr Gln Thr Pro Asp Ile Ile Cys His Arg
65                  70                  75                  80

Gly Ala Lys Pro Gly Ala Leu Thr Ala Pro Val Ser Pro Gly Gly Thr
                85                  90                  95

-continued

```
Val Glu Leu Gln Trp Thr Pro Trp Pro Asp Ser His His Gly Pro Val
                100                 105                 110

Ile Asn Tyr Leu Ala Pro Cys Asn Gly Asp Cys Ser Thr Val Asp Lys
            115                 120                 125

Thr Gln Leu Glu Phe Phe Lys Ile Ala Glu Ser Gly Leu Ile Asn Asp
        130                 135                 140

Asp Asn Pro Pro Gly Ile Trp Ala Ser Asp Asn Leu Ile Ala Ala Asn
145                 150                 155                 160

Asn Ser Trp Thr Val Thr Ile Pro Thr Thr Ile Ala Pro Gly Asn Tyr
                165                 170                 175

Val Leu Arg His Glu Ile Ile Ala Leu His Ser Ala Gln Asn Gln Asp
            180                 185                 190

Gly Ala Gln Asn Tyr Pro Gln Cys Ile Asn Leu Gln Val Thr Gly Gly
        195                 200                 205

Gly Ser Asp Asn Pro Ala Gly Thr Leu Gly Thr Ala Leu Tyr His Asp
210                 215                 220

Thr Asp Pro Gly Ile Leu Ile Asn Ile Tyr Gln Lys Leu Ser Ser Tyr
225                 230                 235                 240

Ile Ile Pro Gly Pro Pro Leu Tyr Thr Gly
                245                 250
```

<210> SEQ ID NO 10
<211> LENGTH: 253
<212> TYPE: PRT
<213> ORGANISM: Penicillium emersonii
<220> FEATURE:
<221> NAME/KEY: SIGNAL
<222> LOCATION: (1)..(25)

<400> SEQUENCE: 10

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205
```

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 11
<211> LENGTH: 618
<212> TYPE: PRT
<213> ORGANISM: Talaromyces emersonii

<400> SEQUENCE: 11

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
65                  70                  75                  80

Trp Thr Arg Asp Ala Ala Leu Thr Ala Lys Tyr Leu Val Asp Ala Phe
                85                  90                  95

Ile Ala Gly Asn Lys Asp Leu Glu Gln Thr Ile Gln Gln Tyr Ile Ser
            100                 105                 110

Ala Gln Ala Lys Val Gln Thr Ile Ser Asn Pro Ser Gly Asp Leu Ser
        115                 120                 125

Thr Gly Gly Leu Gly Glu Pro Lys Phe Asn Val Asn Glu Thr Ala Phe
130                 135                 140

Thr Gly Pro Trp Gly Arg Pro Gln Arg Asp Gly Pro Ala Leu Arg Ala
145                 150                 155                 160

Thr Ala Leu Ile Ala Tyr Ala Asn Tyr Leu Ile Asp Asn Gly Glu Ala
                165                 170                 175

Ser Thr Ala Asp Glu Ile Ile Trp Pro Ile Val Gln Asn Asp Leu Ser
            180                 185                 190

Tyr Ile Thr Gln Tyr Trp Asn Ser Ser Thr Phe Asp Leu Trp Glu Glu
        195                 200                 205

Val Glu Gly Ser Ser Phe Phe Thr Thr Ala Val Gln His Arg Ala Leu
210                 215                 220

Val Glu Gly Asn Ala Leu Ala Thr Arg Leu Asn His Thr Cys Ser Asn
225                 230                 235                 240

Cys Val Ser Gln Ala Pro Gln Val Leu Cys Phe Leu Gln Ser Tyr Trp
                245                 250                 255

Thr Gly Ser Tyr Val Leu Ala Asn Phe Gly Gly Ser Gly Arg Ser Gly
            260                 265                 270

Lys Asp Val Asn Ser Ile Leu Gly Ser Ile His Thr Phe Asp Pro Ala
        275                 280                 285

Gly Gly Cys Asp Asp Ser Thr Phe Gln Pro Cys Ser Ala Arg Ala Leu
290                 295                 300

Ala Asn His Lys Val Val Thr Asp Ser Phe Arg Ser Ile Tyr Ala Ile
305                 310                 315                 320

Asn Ser Gly Ile Ala Glu Gly Ser Ala Val Ala Val Gly Arg Tyr Pro

```
                        325                 330                 335
Glu Asp Val Tyr Gln Gly Gly Asn Pro Trp Tyr Leu Ala Thr Ala Ala
            340                 345                 350

Ala Ala Glu Gln Leu Tyr Asp Ala Ile Tyr Gln Trp Lys Lys Ile Gly
        355                 360                 365

Ser Ile Ser Ile Thr Asp Val Ser Leu Pro Phe Phe Gln Asp Ile Tyr
    370                 375                 380

Pro Ser Ala Ala Val Gly Thr Tyr Asn Ser Gly Ser Thr Thr Phe Asn
385                 390                 395                 400

Asp Ile Ile Ser Ala Val Gln Thr Tyr Gly Asp Gly Tyr Leu Ser Ile
                405                 410                 415

Val Glu Lys Tyr Thr Pro Ser Asp Gly Ser Leu Thr Glu Gln Phe Ser
            420                 425                 430

Arg Thr Asp Gly Thr Pro Leu Ser Ala Ser Ala Leu Thr Trp Ser Tyr
        435                 440                 445

Ala Ser Leu Leu Thr Ala Ser Ala Arg Arg Gln Ser Val Val Pro Ala
    450                 455                 460

Ser Trp Gly Glu Ser Ser Ala Ser Ser Val Pro Ala Val Cys Ser Ala
465                 470                 475                 480

Thr Ser Ala Thr Gly Pro Tyr Ser Thr Ala Thr Asn Thr Val Trp Pro
                485                 490                 495

Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 12
<211> LENGTH: 574
<212> TYPE: PRT
<213> ORGANISM: Trametes cingulata

<400> SEQUENCE: 12

Met Arg Phe Thr Leu Leu Thr Ser Leu Leu Gly Leu Ala Leu Gly Ala
1               5                   10                  15

Phe Ala Gln Ser Ser Ala Ala Asp Ala Tyr Val Ala Ser Glu Ser Pro
            20                  25                  30

Ile Ala Lys Ala Gly Val Leu Ala Asn Ile Gly Pro Ser Gly Ser Lys
        35                  40                  45

Ser Asn Gly Ala Lys Ala Gly Ile Val Ile Ala Ser Pro Ser Thr Ser
    50                  55                  60

Asn Pro Asn Tyr Leu Tyr Thr Trp Thr Arg Asp Ser Ser Leu Val Phe
65                  70                  75                  80
```

```
Lys Ala Leu Ile Asp Gln Phe Thr Thr Gly Glu Asp Thr Ser Leu Arg
                85                  90                  95
Thr Leu Ile Asp Glu Phe Thr Ser Ala Glu Ala Ile Leu Gln Gln Val
            100                 105                 110
Pro Asn Pro Ser Gly Thr Val Ser Thr Gly Gly Leu Gly Glu Pro Lys
            115                 120                 125
Phe Asn Ile Asp Glu Thr Ala Phe Thr Asp Ala Trp Gly Arg Pro Gln
            130                 135                 140
Arg Asp Gly Pro Ala Leu Arg Ala Thr Ala Ile Ile Thr Tyr Ala Asn
145                 150                 155                 160
Trp Leu Leu Asp Asn Lys Asn Thr Thr Tyr Val Thr Asn Thr Leu Trp
                165                 170                 175
Pro Ile Ile Lys Leu Asp Leu Asp Tyr Val Ala Ser Asn Trp Asn Gln
                180                 185                 190
Ser Thr Phe Asp Leu Trp Glu Glu Ile Asn Ser Ser Ser Phe Phe Thr
            195                 200                 205
Thr Ala Val Gln His Arg Ala Leu Arg Glu Gly Ala Thr Phe Ala Asn
            210                 215                 220
Arg Ile Gly Gln Thr Ser Val Val Ser Gly Tyr Thr Thr Gln Ala Asn
225                 230                 235                 240
Asn Leu Leu Cys Phe Leu Gln Ser Tyr Trp Asn Pro Thr Gly Gly Tyr
                245                 250                 255
Ile Thr Ala Asn Thr Gly Gly Gly Arg Ser Gly Lys Asp Ala Asn Thr
                260                 265                 270
Val Leu Thr Ser Ile His Thr Phe Asp Pro Ala Ala Gly Cys Asp Ala
                275                 280                 285
Val Thr Phe Gln Pro Cys Ser Asp Lys Ala Leu Ser Asn Leu Lys Val
            290                 295                 300
Tyr Val Asp Ala Phe Arg Ser Ile Tyr Ser Ile Asn Ser Gly Ile Ala
305                 310                 315                 320
Ser Asn Ala Ala Val Ala Thr Gly Arg Tyr Pro Glu Asp Ser Tyr Met
                325                 330                 335
Gly Gly Asn Pro Trp Tyr Leu Thr Thr Ser Ala Val Ala Glu Gln Leu
            340                 345                 350
Tyr Asp Ala Leu Ile Val Trp Asn Lys Leu Gly Ala Leu Asn Val Thr
            355                 360                 365
Ser Thr Ser Leu Pro Phe Phe Gln Gln Phe Ser Ser Gly Val Thr Val
            370                 375                 380
Gly Thr Tyr Ala Ser Ser Ser Thr Phe Lys Thr Leu Thr Ser Ala
385                 390                 395                 400
Ile Lys Thr Phe Ala Asp Gly Phe Leu Ala Val Asn Ala Lys Tyr Thr
                405                 410                 415
Pro Ser Asn Gly Gly Leu Ala Glu Gln Tyr Ser Arg Ser Asn Gly Ser
            420                 425                 430
Pro Val Ser Ala Val Asp Leu Thr Trp Ser Tyr Ala Ala Ala Leu Thr
            435                 440                 445
Ser Phe Ala Ala Arg Ser Gly Lys Thr Tyr Ala Ser Trp Gly Ala Ala
            450                 455                 460
Gly Leu Thr Val Pro Thr Thr Cys Ser Gly Ser Gly Gly Ala Gly Thr
465                 470                 475                 480
Val Ala Val Thr Phe Asn Val Gln Ala Thr Thr Val Phe Gly Glu Asn
                485                 490                 495
Ile Tyr Ile Thr Gly Ser Val Pro Ala Leu Gln Asn Trp Ser Pro Asp
```

```
                    500                 505                 510
Asn Ala Leu Ile Leu Ser Ala Ala Asn Tyr Pro Thr Trp Ser Ile Thr
                515                 520                 525

Val Asn Leu Pro Ala Ser Thr Thr Ile Glu Tyr Lys Tyr Ile Arg Lys
530                 535                 540

Phe Asn Gly Ala Val Thr Trp Glu Ser Asp Pro Asn Asn Ser Ile Thr
545                 550                 555                 560

Thr Pro Ala Ser Gly Thr Phe Thr Gln Asn Asp Thr Trp Arg
                565                 570

<210> SEQ ID NO 13
<211> LENGTH: 583
<212> TYPE: PRT
<213> ORGANISM: Rhizomucor pusillus

<400> SEQUENCE: 13

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
                20                  25                  30

Ser Asn Tyr Cys Gly Gly Thr Tyr Glu Gly Ile Thr Lys His Leu Asp
            35                  40                  45

Tyr Ile Ser Gly Met Gly Phe Asp Ala Ile Trp Ile Ser Pro Ile Pro
        50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
                100                 105                 110

Asn His Ala Gly Pro Thr Ser Asn Gly Tyr Ser Gly Tyr Thr Phe Gly
            115                 120                 125

Asp Ala Ser Leu Tyr His Pro Lys Cys Thr Ile Asp Tyr Asn Asp Gln
        130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
                180                 185                 190

His Ile Arg Lys Asp Phe Trp Thr Gly Tyr Ala Glu Ala Ala Gly Val
            195                 200                 205

Phe Ala Thr Gly Glu Val Phe Asn Gly Asp Pro Ala Tyr Val Gly Pro
        210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
                260                 265                 270

Thr Thr Phe Val Asp Asn His Asp Asn Pro Arg Phe Leu Asn Ser Gln
            275                 280                 285

Ser Asp Lys Ala Leu Phe Lys Asn Ala Leu Thr Tyr Val Leu Leu Gly
        290                 295                 300
```

```
Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
            325                 330                 335

Thr Ser Ser Asp Leu Tyr Gln Phe Ile Lys Thr Val Asn Ser Val Arg
        340                 345                 350

Met Lys Ser Asn Lys Ala Val Tyr Met Asp Ile Tyr Val Gly Asp Asn
    355                 360                 365

Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
            405                 410                 415

Val Ser Ser Asp Gly Thr Val Thr Phe Asn Leu Lys Asp Gly Leu Pro
        420                 425                 430

Ala Ile Phe Thr Ser Ala Thr Gly Gly Thr Thr Thr Ala Thr Pro
    435                 440                 445

Thr Gly Ser Gly Ser Val Thr Ser Thr Ser Lys Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
        515                 520                 525

Leu Trp Tyr Val Thr Val Thr Leu Pro Ala Gly Glu Ser Phe Glu Tyr
        530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 14
<211> LENGTH: 661
<212> TYPE: PRT
<213> ORGANISM: Trichoderma reesei

<400> SEQUENCE: 14

Leu Tyr Ile Asn Gly Ser Val Ile Ala Pro Cys Asp Ser Pro Ile Tyr
1               5                   10                  15

Cys His Gly Asp Ile Leu Arg Glu Ile Glu Leu Ala His Pro Phe Ser
            20                  25                  30

Asp Ser Lys Thr Phe Val Asp Met Pro Ala Lys Arg Pro Leu Ser Glu
        35                  40                  45

Ile Gln Thr Ala Phe Ala Asn Leu Pro Lys Pro Leu Arg Asn Asp Ser
    50                  55                  60

Ser Leu Gln Thr Phe Leu Ala Ser Tyr Phe Ala Asp Ala Gly Gly Glu
65                  70                  75                  80

Leu Ile Gln Val Pro Arg Ala Asn Leu Thr Thr Asn Pro Thr Phe Leu
                85                  90                  95
```

```
Ser Lys Ile Asn Asp Thr Val Ile Glu Gln Phe Val Thr Gln Val Ile
            100                 105                 110

Asp Ile Trp Pro Asp Leu Thr Arg Arg Tyr Ala Gly Asp Ala Ala Val
            115                 120                 125

Lys Asn Cys Ser Ser Cys Pro Asn Ser Phe Ile Pro Val Asn Arg Thr
130                 135                 140

Phe Val Val Ala Gly Gly Arg Phe Arg Glu Pro Tyr Tyr Trp Asp Ser
145                 150                 155                 160

Tyr Trp Ile Val Glu Gly Leu Leu Arg Thr Gly Gly Ala Phe Val Gly
            165                 170                 175

Ile Ala Arg Asn Thr Ile Asp Asn Phe Leu Asp Phe Ile Glu Arg Phe
            180                 185                 190

Gly Phe Val Pro Asn Gly Ala Arg Leu Tyr Tyr Leu Asn Arg Ser Gln
            195                 200                 205

Pro Pro Leu Leu Ser Arg Met Val Lys Val Tyr Ile Asp His Thr Asn
            210                 215                 220

Asp Thr Ala Ile Leu Arg Arg Ala Leu Pro Leu Val Lys Glu His
225                 230                 235                 240

Glu Phe Trp Thr Arg Asn Arg Thr Val Asp Val Arg Val Asn Asn Lys
            245                 250                 255

Thr Tyr Val Leu Asn Gln Tyr Ala Val Gln Asn Thr Gln Pro Arg Pro
            260                 265                 270

Glu Ser Phe Arg Glu Asp Phe Gln Thr Ala Asn Asn Arg Ser Tyr Tyr
            275                 280                 285

Ala Ala Ser Gly Ile Ile Tyr Pro Ala Thr Lys Pro Leu Asn Glu Ser
            290                 295                 300

Gln Ile Glu Glu Leu Tyr Ala Asn Leu Ala Ser Gly Ala Glu Ser Gly
305                 310                 315                 320

Asn Asp Tyr Thr Ala Arg Trp Leu Ala Asp Pro Ser Asp Ala Met Arg
            325                 330                 335

Asp Val Tyr Phe Pro Leu Arg Ser Leu Asn Asn Lys Asp Ile Val Pro
            340                 345                 350

Val Asp Leu Asn Ser Ile Leu Tyr Gly Asn Glu Leu Ala Ile Ala Gln
            355                 360                 365

Phe Tyr Asn Gln Thr Gly Asn Thr Thr Ala Ala Arg Glu Trp Ser Ser
            370                 375                 380

Leu Ala Ala Asn Arg Ser Ala Ser Ile Gln Ala Val Phe Trp Asn Glu
385                 390                 395                 400

Thr Leu Phe Ser Tyr Phe Asp Tyr Asn Leu Thr Ser Ser Ser Gln Asn
            405                 410                 415

Ile Tyr Val Pro Leu Asp Lys Asp Ala Val Ala Leu Asp Arg Gln Thr
            420                 425                 430

Ala Pro Pro Gly Lys Gln Val Leu Phe His Val Gly Gln Phe Tyr Pro
            435                 440                 445

Phe Trp Thr Gly Ala Ala Pro Glu Tyr Leu Arg Asn Asn Pro Phe Ala
            450                 455                 460

Val Thr Arg Ile Phe Asp Arg Val Lys Ser Tyr Leu Asp Thr Arg Pro
465                 470                 475                 480

Gly Gly Ile Pro Ala Ser Asn Val Asn Thr Gly Gln Gln Trp Asp Gln
            485                 490                 495

Pro Asn Val Trp Pro Pro His Met His Ile Leu Met Glu Ser Leu Asn
            500                 505                 510
```

-continued

```
Ser Val Pro Ala Thr Phe Ser Glu Ala Asp Pro Ala Tyr Gln Asp Val
        515                 520                 525

Arg Asn Leu Ser Leu Arg Leu Gly Gln Arg Tyr Leu Asp Phe Thr Phe
    530                 535                 540

Cys Thr Trp Arg Ala Thr Gly Gly Ser Thr Ser Glu Thr Pro Lys Leu
545                 550                 555                 560

Gln Gly Leu Thr Asp Gln Asp Val Gly Ile Met Phe Glu Lys Tyr Asn
                565                 570                 575

Asp Asn Ser Thr Asn Ala Ala Gly Gly Gly Glu Tyr Gln Val Val
                580                 585                 590

Glu Gly Phe Gly Trp Thr Asn Gly Val Leu Leu Trp Thr Ala Asp Thr
                595                 600                 605

Phe Gly Ser Gln Leu Lys Arg Pro Gln Cys Gly Asn Ile Met Ala Gly
    610                 615                 620

His Pro Ala Pro Ser Lys Arg Ser Ala Val Gln Leu Asp Met Trp Asp
625                 630                 635                 640

Ala Ser Arg Val Lys Lys Phe Gly Arg Arg Ala Glu Gly Arg Met Gly
                645                 650                 655

Thr Leu His Ala Trp
                660
```

<210> SEQ ID NO 15
<211> LENGTH: 862
<212> TYPE: PRT
<213> ORGANISM: Bacillus sp.
<220> FEATURE:
<221> NAME/KEY: SIGNAL
<222> LOCATION: (1)..(33)

<400> SEQUENCE: 15

```
Met Ser Leu Ile Arg Ser Arg Tyr Asn His Phe Val Ile Leu Phe Thr
1               5                   10                  15

Val Ala Ile Met Phe Leu Thr Val Cys Phe Pro Ala Tyr Lys Ala Leu
                20                  25                  30

Ala Asp Ser Thr Ser Thr Glu Val Ile Val His Tyr His Arg Phe Asp
            35                  40                  45

Ser Asn Tyr Ala Asn Trp Asp Leu Trp Met Trp Pro Tyr Gln Pro Val
    50                  55                  60

Asn Gly Asn Gly Ala Ala Tyr Glu Phe Ser Gly Lys Asp Asp Phe Gly
65                  70                  75                  80

Val Lys Ala Asp Val Gln Val Pro Gly Asp Asp Thr Gln Val Gly Leu
                85                  90                  95

Ile Val Arg Thr Asn Asp Trp Ser Gln Lys Asn Thr Ser Asp Asp Leu
                100                 105                 110

His Ile Asp Leu Thr Lys Gly His Glu Ile Trp Ile Val Gln Gly Asp
            115                 120                 125

Pro Asn Ile Tyr Tyr Asn Leu Ser Asp Ala Gln Ala Ala Thr Pro
    130                 135                 140

Lys Val Ser Asn Ala Tyr Leu Asp Asn Glu Lys Thr Val Leu Ala Lys
145                 150                 155                 160

Leu Thr Asn Pro Met Thr Leu Ser Asp Gly Ser Ser Gly Phe Thr Val
                165                 170                 175

Thr Asp Lys Thr Thr Gly Glu Gln Ile Pro Val Thr Ala Ala Thr Asn
            180                 185                 190

Ala Asn Ser Ala Ser Ser Ser Glu Gln Thr Asp Leu Val Gln Leu Thr
    195                 200                 205
```

```
Leu Ala Ser Ala Pro Asp Val Ser His Thr Ile Gln Val Gly Ala Ala
    210                 215                 220
Gly Tyr Glu Ala Val Asn Leu Ile Pro Arg Asn Val Leu Asn Leu Pro
225                 230                 235                 240
Arg Tyr Tyr Tyr Ser Gly Asn Asp Leu Gly Asn Val Tyr Ser Asn Lys
                245                 250                 255
Ala Thr Ala Phe Arg Val Trp Ala Pro Thr Ala Ser Asp Val Gln Leu
            260                 265                 270
Leu Leu Tyr Asn Ser Glu Thr Gly Pro Val Thr Lys Gln Leu Glu Met
        275                 280                 285
Gln Lys Ser Asp Asn Gly Thr Trp Lys Leu Lys Val Pro Gly Asn Leu
    290                 295                 300
Lys Asn Trp Tyr Tyr Leu Tyr Gln Val Thr Val Asn Gly Lys Thr Gln
305                 310                 315                 320
Thr Ala Val Asp Pro Tyr Val Arg Ala Ile Ser Val Asn Ala Thr Arg
                325                 330                 335
Gly Met Ile Val Asp Leu Glu Asp Thr Asn Pro Pro Gly Trp Lys Glu
            340                 345                 350
Asp His Gln Gln Thr Pro Ala Asn Pro Val Asp Glu Val Ile Tyr Glu
        355                 360                 365
Val His Val Arg Asp Phe Ser Ile Asp Ala Asn Ser Gly Met Lys Asn
    370                 375                 380
Lys Gly Lys Tyr Leu Ala Phe Thr Glu His Gly Thr Lys Gly Pro Asp
385                 390                 395                 400
Asn Val Lys Thr Gly Ile Asp Ser Leu Lys Glu Leu Gly Ile Asn Ala
                405                 410                 415
Val Gln Leu Gln Pro Ile Glu Glu Phe Asn Ser Ile Asp Glu Thr Gln
            420                 425                 430
Pro Asn Met Tyr Asn Trp Gly Tyr Asp Pro Arg Asn Tyr Asn Val Pro
        435                 440                 445
Glu Gly Ala Tyr Ala Thr Thr Pro Glu Gly Thr Ala Arg Ile Thr Gln
    450                 455                 460
Leu Lys Gln Leu Ile Gln Ser Ile His Lys Asp Arg Ile Ala Ile Asn
465                 470                 475                 480
Met Asp Val Val Tyr Asn His Thr Phe Asn Val Gly Val Ser Asp Phe
                485                 490                 495
Asp Lys Ile Val Pro Gln Tyr Tyr Arg Thr Asp Ser Ala Gly Asn
            500                 505                 510
Tyr Thr Asn Gly Ser Gly Val Gly Asn Glu Ile Ala Thr Glu Arg Pro
        515                 520                 525
Met Val Gln Lys Phe Val Leu Asp Ser Val Lys Tyr Trp Val Lys Glu
    530                 535                 540
Tyr His Ile Asp Gly Phe Arg Phe Asp Leu Met Ala Leu Leu Gly Lys
545                 550                 555                 560
Asp Thr Met Ala Lys Ile Ser Lys Glu Leu His Ala Ile Asn Pro Gly
                565                 570                 575
Ile Val Leu Tyr Gly Glu Pro Trp Thr Gly Gly Thr Ser Gly Leu Ser
            580                 585                 590
Ser Asp Gln Leu Val Thr Lys Gly Gln Gln Lys Gly Leu Gly Ile Gly
        595                 600                 605
Val Phe Asn Asp Asn Ile Arg Asn Gly Leu Asp Gly Asn Val Phe Asp
    610                 615                 620
```

```
Lys Ser Ala Gln Gly Phe Ala Thr Gly Asp Pro Asn Gln Val Asn Val
625                 630                 635                 640

Ile Lys Asn Gly Val Met Gly Ser Ile Ser Asp Phe Thr Ser Ala Pro
            645                 650                 655

Ser Glu Thr Ile Asn Tyr Val Thr Ser His Asp Asn Met Thr Leu Trp
                660                 665                 670

Asp Lys Ile Ser Ala Ser Asn Pro Asn Asp Thr Gln Ala Asp Arg Ile
            675                 680                 685

Lys Met Asp Glu Leu Ala Gln Ala Val Val Phe Thr Ser Gln Gly Val
690                 695                 700

Pro Phe Met Gln Gly Gly Glu Glu Met Leu Arg Thr Lys Gly Gly Asn
705                 710                 715                 720

Asp Asn Ser Tyr Asn Ala Gly Asp Ser Val Asn Gln Phe Asp Trp Ser
                725                 730                 735

Arg Lys Ala Gln Phe Glu Asn Val Phe Asp Tyr Tyr Ser Trp Leu Ile
                740                 745                 750

His Leu Arg Asp Asn His Pro Ala Phe Arg Met Thr Thr Ala Asp Gln
            755                 760                 765

Ile Lys Gln Asn Leu Thr Phe Leu Asp Ser Pro Thr Asn Thr Val Ala
770                 775                 780

Phe Glu Leu Lys Asn His Ala Asn His Asp Lys Trp Lys Asn Ile Ile
785                 790                 795                 800

Val Met Tyr Asn Pro Asn Lys Thr Ala Gln Thr Leu Thr Leu Pro Ser
                805                 810                 815

Gly Asn Trp Thr Ile Val Gly Leu Gly Asn Gln Val Gly Glu Lys Ser
                820                 825                 830

Leu Gly His Val Asn Gly Thr Val Glu Val Pro Ala Leu Ser Thr Ile
            835                 840                 845

Ile Leu His Gln Gly Thr Ser Glu Asp Val Ile Asp Gln Asn
850                 855                 860

<210> SEQ ID NO 16
<211> LENGTH: 616
<212> TYPE: PRT
<213> ORGANISM: Penicillium oxalicum

<400> SEQUENCE: 16

Met Arg Leu Thr Leu Leu Ser Gly Val Ala Gly Val Leu Cys Ala Gly
1               5                   10                  15

Gln Leu Thr Ala Ala Arg Pro Asp Pro Lys Gly Gly Asn Leu Thr Pro
                20                  25                  30

Phe Ile His Lys Glu Gly Glu Arg Ser Leu Gln Gly Ile Leu Asp Asn
            35                  40                  45

Leu Gly Gly Arg Gly Lys Lys Thr Pro Gly Thr Ala Ala Gly Leu Phe
        50                  55                  60

Ile Ala Ser Pro Asn Thr Glu Asn Pro Asn Tyr Tyr Tyr Thr Trp Thr
65                  70                  75                  80

Arg Asp Ser Ala Leu Thr Ala Lys Cys Leu Ile Asp Leu Phe Glu Asp
                85                  90                  95

Ser Arg Ala Lys Phe Pro Ile Asp Arg Lys Tyr Leu Glu Thr Gly Ile
                100                 105                 110

Arg Asp Tyr Val Ser Ser Gln Ala Ile Leu Gln Ser Val Ser Asn Pro
            115                 120                 125

Ser Gly Thr Leu Lys Asp Gly Ser Gly Leu Gly Glu Pro Lys Phe Glu
        130                 135                 140
```

```
Ile Asp Leu Asn Pro Phe Ser Gly Ala Trp Gly Arg Pro Gln Arg Asp
145                 150                 155                 160

Gly Pro Ala Leu Arg Ala Thr Ala Met Ile Thr Tyr Ala Asn Tyr Leu
            165                 170                 175

Ile Ser His Gly Gln Lys Ser Asp Val Ser Gln Val Met Trp Pro Ile
            180                 185                 190

Ile Ala Asn Asp Leu Ala Tyr Val Gly Gln Tyr Trp Asn Asn Thr Gly
            195                 200                 205

Phe Asp Leu Trp Glu Glu Val Asp Gly Ser Ser Phe Phe Thr Ile Ala
210                 215                 220

Val Gln His Arg Ala Leu Val Glu Gly Ser Gln Leu Ala Lys Lys Leu
225                 230                 235                 240

Gly Lys Ser Cys Asp Ala Cys Asp Ser Gln Pro Pro Gln Ile Leu Cys
            245                 250                 255

Phe Leu Gln Ser Phe Trp Asn Gly Lys Tyr Ile Thr Ser Asn Ile Asn
            260                 265                 270

Thr Gln Ala Ser Arg Ser Gly Ile Asp Leu Asp Ser Val Leu Gly Ser
            275                 280                 285

Ile His Thr Phe Asp Pro Glu Ala Ala Cys Asp Asp Ala Thr Phe Gln
290                 295                 300

Pro Cys Ser Ala Arg Ala Leu Ala Asn His Lys Val Tyr Val Asp Ser
305                 310                 315                 320

Phe Arg Ser Ile Tyr Lys Ile Asn Ala Gly Leu Ala Glu Gly Ser Ala
                325                 330                 335

Ala Asn Val Gly Arg Tyr Pro Glu Asp Val Tyr Gln Gly Gly Asn Pro
            340                 345                 350

Trp Tyr Leu Ala Thr Leu Gly Ala Ser Glu Leu Leu Tyr Asp Ala Leu
            355                 360                 365

Tyr Gln Trp Asp Arg Leu Gly Lys Leu Glu Val Ser Glu Thr Ser Leu
370                 375                 380

Ser Phe Phe Lys Asp Phe Asp Ala Thr Val Lys Ile Gly Ser Tyr Ser
385                 390                 395                 400

Arg Asn Ser Lys Thr Tyr Lys Lys Leu Thr Gln Ser Ile Lys Ser Tyr
                405                 410                 415

Ala Asp Gly Phe Ile Gln Leu Val Gln Gln Tyr Thr Pro Ser Asn Gly
            420                 425                 430

Ser Leu Ala Glu Gln Tyr Asp Arg Asn Thr Ala Ala Pro Leu Ser Ala
            435                 440                 445

Asn Asp Leu Thr Trp Ser Phe Ala Ser Phe Leu Thr Ala Thr Gln Arg
450                 455                 460

Arg Asp Ala Val Val Pro Pro Ser Trp Gly Ala Lys Ser Ala Asn Lys
465                 470                 475                 480

Val Pro Thr Thr Cys Ser Ala Ser Pro Val Val Gly Thr Tyr Lys Ala
                485                 490                 495

Pro Thr Ala Thr Phe Ser Ser Lys Thr Lys Cys Val Pro Ala Lys Asp
            500                 505                 510

Ile Val Pro Ile Thr Phe Tyr Leu Ile Glu Asn Thr Tyr Tyr Gly Glu
            515                 520                 525

Asn Val Phe Met Ser Gly Asn Ile Thr Ala Leu Gly Asn Trp Asp Ala
            530                 535                 540

Lys Lys Gly Phe Pro Leu Thr Ala Asn Leu Tyr Thr Gln Asp Gln Asn
545                 550                 555                 560
```

```
Leu Trp Phe Ala Ser Val Glu Phe Ile Pro Ala Gly Thr Pro Phe Glu
                565                 570                 575

Tyr Lys Tyr Tyr Lys Val Glu Pro Asn Gly Asp Ile Thr Trp Glu Lys
            580                 585                 590

Gly Pro Asn Arg Val Phe Val Ala Pro Thr Gly Cys Pro Val Gln Pro
            595                 600                 605

His Ser Asn Asp Val Trp Gln Phe
610                 615

<210> SEQ ID NO 17
<211> LENGTH: 573
<212> TYPE: PRT
<213> ORGANISM: Pycnoporus sanguineus
<220> FEATURE:
<221> NAME/KEY: SIGNAL
<222> LOCATION: (1)..(18)

<400> SEQUENCE: 17

Met Arg Phe Thr Leu Leu Ala Ser Leu Ile Gly Leu Ala Val Gly Ala
1               5                   10                  15

Phe Ala Gln Ser Ser Ala Val Asp Ala Tyr Val Ala Ser Glu Ser Pro
                20                  25                  30

Ile Ala Lys Gln Gly Val Leu Asn Asn Ile Gly Pro Asn Gly Ser Lys
            35                  40                  45

Ala His Gly Ala Lys Ala Gly Ile Val Val Ala Ser Pro Ser Thr Glu
    50                  55                  60

Asn Pro Asp Tyr Leu Tyr Thr Trp Thr Arg Asp Ser Ser Leu Val Phe
65                  70                  75                  80

Lys Leu Leu Ile Asp Gln Phe Thr Ser Gly Asp Asp Thr Ser Leu Arg
                85                  90                  95

Gly Leu Ile Asp Asp Phe Thr Ser Ala Glu Ala Ile Leu Gln Gln Val
            100                 105                 110

Ser Asn Pro Ser Gly Thr Val Ser Thr Gly Gly Leu Gly Glu Pro Lys
        115                 120                 125

Phe Asn Ile Asp Glu Thr Ala Phe Thr Gly Ala Trp Gly Arg Pro Gln
    130                 135                 140

Arg Asp Gly Pro Ala Leu Arg Ala Thr Ser Ile Ile Arg Tyr Ala Asn
145                 150                 155                 160

Trp Leu Leu Asp Asn Gly Asn Thr Thr Tyr Val Ser Asn Thr Leu Trp
                165                 170                 175

Pro Val Ile Gln Leu Asp Leu Asp Tyr Val Ala Asp Asn Trp Asn Gln
            180                 185                 190

Ser Thr Phe Asp Leu Trp Glu Glu Val Asp Ser Ser Phe Phe Thr
        195                 200                 205

Thr Ala Val Gln His Arg Ala Leu Arg Glu Gly Ala Thr Phe Ala Ser
    210                 215                 220

Arg Ile Gly Gln Ser Ser Val Val Ser Gly Tyr Thr Thr Gln Ala Asp
225                 230                 235                 240

Asn Leu Leu Cys Phe Leu Gln Ser Tyr Trp Asn Pro Ser Gly Gly Tyr
                245                 250                 255

Val Thr Ala Asn Thr Gly Gly Gly Arg Ser Gly Lys Asp Ser Asn Thr
            260                 265                 270

Val Leu Thr Ser Ile His Thr Phe Asp Pro Ala Ala Gly Cys Asp Ala
        275                 280                 285

Ala Thr Phe Gln Pro Cys Ser Asp Lys Ala Leu Ser Asn Leu Lys Val
    290                 295                 300
```

```
Tyr Val Asp Ala Phe Arg Ser Ile Tyr Thr Ile Asn Asn Gly Ile Ala
305                 310                 315                 320

Ser Asn Ala Ala Val Ala Thr Gly Arg Tyr Pro Glu Asp Ser Tyr Met
            325                 330                 335

Gly Gly Asn Pro Trp Tyr Leu Thr Thr Ser Ala Val Ala Glu Gln Leu
        340                 345                 350

Tyr Asp Ala Leu Tyr Val Trp Asp Gln Leu Gly Gly Leu Asn Val Thr
            355                 360                 365

Ser Thr Ser Leu Ala Phe Phe Gln Gln Phe Ala Ser Gly Leu Ser Thr
370                 375                 380

Gly Thr Tyr Ser Ala Ser Ser Thr Tyr Ala Thr Leu Thr Ser Ala
385                 390                 395                 400

Ile Arg Ser Phe Ala Asp Gly Phe Leu Ala Ile Asn Ala Lys Tyr Thr
                405                 410                 415

Pro Ala Asp Gly Gly Leu Ala Glu Gln Tyr Ser Arg Asn Asp Gly Thr
            420                 425                 430

Pro Leu Ser Ala Val Asp Leu Thr Trp Ser Tyr Ala Ala Ala Leu Thr
        435                 440                 445

Ala Phe Ala Ala Arg Glu Gly Lys Thr Tyr Gly Ser Trp Gly Ala Ala
    450                 455                 460

Gly Leu Thr Val Pro Ala Ser Cys Ser Gly Gly Gly Ala Thr Val
465                 470                 475                 480

Ala Val Thr Phe Asn Val Gln Ala Thr Val Phe Gly Glu Asn Ile
                485                 490                 495

Tyr Ile Thr Gly Ser Val Ala Ala Leu Gln Asn Trp Ser Pro Asp Asn
            500                 505                 510

Ala Leu Ile Leu Ser Ala Ala Asn Tyr Pro Thr Trp Ser Ile Thr Val
        515                 520                 525

Asn Leu Pro Ala Asn Thr Val Val Gln Tyr Lys Tyr Ile Arg Lys Phe
    530                 535                 540

Asn Gly Gln Val Thr Trp Glu Ser Asp Pro Asn Asn Gln Ile Thr Thr
545                 550                 555                 560

Pro Ser Gly Gly Ser Phe Thr Gln Asn Asp Val Trp Arg
                565                 570

<210> SEQ ID NO 18
<211> LENGTH: 576
<212> TYPE: PRT
<213> ORGANISM: Gloephyllum trabeum
<220> FEATURE:
<221> NAME/KEY: SIGNAL
<222> LOCATION: (1)..(17)
<220> FEATURE:
<221> NAME/KEY: mat_peptide
<222> LOCATION: (18)..(576)

<400> SEQUENCE: 18

Met Tyr Arg Phe Leu Val Cys Ala Leu Gly Leu Leu Gly Thr Val Leu
        -15                 -10                 -5

Ala Gln Ser Val Asp Ser Tyr Val Gly Ser Glu Gly Pro Ile Ala Lys
-1   1               5                  10                  15

Ala Gly Val Leu Ala Asn Ile Gly Pro Asn Gly Ser Lys Ala Ser Gly
                20                  25                  30

Ala Ala Ala Gly Val Val Val Ala Ser Pro Ser Lys Ser Asp Pro Asp
            35                  40                  45

Tyr Trp Tyr Thr Trp Thr Arg Asp Ser Ser Leu Val Phe Lys Ser Leu
```

```
                50                  55                  60
Ile Asp Gln Tyr Thr Thr Gly Ile Asp Ser Thr Ser Ser Leu Arg Ser
 65                  70                  75
Leu Ile Asp Ser Phe Val Ile Ala Glu Ala Asn Ile Gln Gln Val Ser
 80                  85                  90                  95
Asn Pro Ser Gly Thr Leu Thr Gly Gly Leu Gly Glu Pro Lys Phe
                100                 105                 110
Asn Val Asp Glu Thr Ala Phe Thr Gly Ala Trp Gly Arg Pro Gln Arg
                115                 120                 125
Asp Gly Pro Ala Leu Arg Ala Thr Ala Leu Ile Thr Tyr Gly Asn Trp
                130                 135                 140
Leu Leu Ser Asn Gly Asn Thr Thr Trp Val Thr Ser Thr Leu Trp Pro
145                 150                 155
Ile Ile Gln Asn Asp Leu Asn Tyr Val Val Gln Tyr Trp Asn Gln Thr
160                 165                 170                 175
Thr Phe Asp Leu Trp Glu Glu Val Asn Ser Ser Ser Phe Phe Thr Thr
                180                 185                 190
Ala Val Gln His Arg Ala Leu Arg Glu Gly Ala Ala Phe Ala Thr Lys
                195                 200                 205
Ile Gly Gln Thr Ser Ser Val Ser Ser Tyr Thr Thr Gln Ala Ala Asn
                210                 215                 220
Leu Leu Cys Phe Leu Gln Ser Tyr Trp Asn Pro Thr Ser Gly Tyr Ile
225                 230                 235
Thr Ala Asn Thr Gly Gly Gly Arg Ser Gly Lys Asp Ala Asn Thr Leu
240                 245                 250                 255
Leu Ala Ser Ile His Thr Tyr Asp Pro Ser Ala Gly Cys Asp Ala Thr
                260                 265                 270
Thr Phe Gln Pro Cys Ser Asp Lys Ala Leu Ser Asn Leu Lys Val Tyr
                275                 280                 285
Val Asp Ser Phe Arg Ser Val Tyr Ser Ile Asn Ser Gly Ile Ala Ser
                290                 295                 300
Asn Ala Ala Val Ala Thr Gly Arg Tyr Pro Glu Asp Ser Tyr Gln Gly
                305                 310                 315
Gly Asn Pro Trp Tyr Leu Thr Thr Phe Ala Val Ala Glu Gln Leu Tyr
320                 325                 330                 335
Asp Ala Leu Asn Val Trp Ala Ala Gln Gly Ser Leu Asn Val Thr Ser
                340                 345                 350
Ile Ser Leu Pro Phe Phe Gln Gln Phe Ser Ser Ser Val Thr Ala Gly
                355                 360                 365
Thr Tyr Ala Ser Ser Ser Thr Thr Tyr Thr Thr Leu Thr Ser Ala Ile
                370                 375                 380
Lys Ser Phe Ala Asp Gly Phe Val Ala Ile Asn Ala Gln Tyr Thr Pro
                385                 390                 395
Ser Asn Gly Gly Leu Ala Glu Gln Phe Ser Arg Ser Asn Gly Ala Pro
400                 405                 410                 415
Val Ser Ala Val Asp Leu Thr Trp Ser Tyr Ala Ser Ala Leu Thr Ala
                420                 425                 430
Phe Glu Ala Arg Asn Asn Thr Gln Phe Ala Gly Trp Gly Ala Val Gly
                435                 440                 445
Leu Thr Val Pro Thr Ser Cys Ser Ser Asn Ser Gly Gly Gly Gly Gly
                450                 455                 460
Ser Thr Val Ala Val Thr Phe Asn Val Asn Ala Gln Thr Val Trp Gly
465                 470                 475
```

```
Glu Asn Ile Tyr Ile Thr Gly Ser Val Asp Ala Leu Ser Asn Trp Ser
480                 485                 490                 495

Pro Asp Asn Ala Leu Leu Ser Ser Ala Asn Tyr Pro Thr Trp Ser
                500                 505                 510

Ile Thr Val Asn Leu Pro Ala Ser Thr Ala Ile Gln Tyr Lys Tyr Ile
                515                 520                 525

Arg Lys Asn Asn Gly Ala Val Thr Trp Glu Ser Asp Pro Asn Asn Ser
                530                 535                 540

Ile Thr Thr Pro Ala Ser Gly Ser Val Thr Glu Asn Asp Thr Trp Arg
545                 550                 555

<210> SEQ ID NO 19
<211> LENGTH: 366
<212> TYPE: PRT
<213> ORGANISM: Meripilus giganteus

<400> SEQUENCE: 19

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
                20                  25                  30

Leu Ala Val Ser Gly Phe Ile Asp Gln Phe Ala Asn Lys Ala Asp Leu
            35                  40                  45

Lys Ser Phe Leu Ala Gln Phe Arg Lys Asp Ile Ser Ser Ser Thr Thr
50              55                  60

Phe Ser Leu Gln Thr Leu Asp Gly Gly Glu Asn Asp Gln Ser Pro Ser
65              70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
                100                 105                 110

Asp Gly Asn Leu Glu Gly Phe Leu Asp Ile Ile Asn Phe Leu Leu Gly
                115                 120                 125

Glu Ser Asn Pro Pro Gln Val Leu Thr Thr Ser Tyr Gly Gln Asn Glu
130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
                180                 185                 190

Phe Pro Ser Gly Cys Pro Phe Met Thr Ser Val Gly Ala Thr Gln Gly
                195                 200                 205

Val Ser Pro Glu Thr Ala Ala Ala Phe Ser Ser Gly Gly Phe Ser Asn
210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
                260                 265                 270

Gly Gly Gln Thr Ile Gly Val Asp Gly Thr Ser Cys Ala Ser Pro Thr
                275                 280                 285

Phe Ala Ser Val Ile Ser Leu Val Asn Asp Arg Leu Ile Ala Ala Gly
```

```
            290                 295                 300
Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
                340                 345                 350

Gly Thr Pro Asn Phe Ala Lys Leu Leu Thr Ala Val Gly Leu
                355                 360                 365

<210> SEQ ID NO 20
<211> LENGTH: 371
<212> TYPE: PRT
<213> ORGANISM: Meripilus giganteus

<400> SEQUENCE: 20

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
                20                  25                  30

Leu Ala Val Ser Gly Phe Ile Asp Gln Phe Ala Asn Lys Ala Asp Leu
            35                  40                  45

Lys Ser Phe Leu Ala Gln Phe Arg Lys Asp Ile Ser Ser Ser Thr Thr
50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
    290                 295                 300
```

-continued

```
Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu Arg His
        355                 360                 365

Gln His Gln
    370
```